(12) United States Patent
Lo

(10) Patent No.: US 12,333,659 B2
(45) Date of Patent: Jun. 17, 2025

(54) SYSTEMS AND METHODS FOR DISPLAYING LAYERED AUGMENTED ANATOMICAL FEATURES

(71) Applicant: Gustav Lo, Petoskey, MI (US)

(72) Inventor: Gustav Lo, Petoskey, MI (US)

( * ) Notice: Subject to any disclaimer, the term of this patent is extended or adjusted under 35 U.S.C. 154(b) by 142 days.

(21) Appl. No.: 18/184,396

(22) Filed: Mar. 15, 2023

(65) Prior Publication Data

US 2023/0290085 A1    Sep. 14, 2023

Related U.S. Application Data

(60) Provisional application No. 63/317,423, filed on Mar. 7, 2022.

(51) Int. Cl.
| | |
|---|---|
| *G06T 19/00* | (2011.01) |
| *G06F 3/14* | (2006.01) |
| *G06V 10/74* | (2022.01) |
| *G06V 20/20* | (2022.01) |
| *G16H 30/40* | (2018.01) |

(52) U.S. Cl.
CPC ............ *G06T 19/006* (2013.01); *G06F 3/14* (2013.01); *G06V 10/761* (2022.01); *G06V 20/20* (2022.01); *G16H 30/40* (2018.01)

(58) Field of Classification Search
USPC ........................................................ 345/633
See application file for complete search history.

(56) References Cited

U.S. PATENT DOCUMENTS

| 10,832,486 | B1 * | 11/2020 | Lo ........................... A61B 90/39 |
| 2011/0082710 | A1 * | 4/2011 | Subash .................. G16H 30/20 |
| | | | 705/3 |

(Continued)

FOREIGN PATENT DOCUMENTS

| CN | 115105204 A | 9/2022 |
| WO | 2022072296 A1 | 4/2022 |

OTHER PUBLICATIONS

Written Opinion of the International Searching Authority for PCT/IB2023/052727, dated Dec. 11, 2023.

(Continued)

*Primary Examiner* — Michael J Cobb
(74) *Attorney, Agent, or Firm* — Miller Johnson

(57) ABSTRACT

A method for displaying a target individual includes receiving a plurality of reference markers that characterize a target individual and selecting a first reference image file and a second reference image file from a database. The method further includes displaying a first graphical representation and a second graphical representation over a visual representation of the target individual. The first reference image file is associated with a first anatomical layer and the second reference image file is associated with a different anatomical layer. The method additionally includes modifying at least one of (i) the first graphical representation or (ii) at least one of the plurality of reference markers. The method also includes displaying, on a display, a modified visual representation of the target individual based on the modified at least one of (i) the first graphical representation or (ii) the at least one of the plurality of reference markers.

21 Claims, 10 Drawing Sheets

(56) References Cited

U.S. PATENT DOCUMENTS

| | | | |
|---|---|---|---|
| 2014/0081659 A1* | 3/2014 | Nawana | G16H 10/20 |
| | | | 705/3 |
| 2016/0038248 A1* | 2/2016 | Bharadwaj | G06T 7/0012 |
| | | | 715/771 |
| 2017/0278301 A1* | 9/2017 | Peterson | G16H 30/40 |
| 2019/0365498 A1 | 12/2019 | Gibby | |
| 2021/0027469 A1* | 1/2021 | Lo | G06T 19/006 |
| 2023/0047622 A1 | 2/2023 | Lax | |
| 2024/0307600 A1* | 9/2024 | Beardsley | G16H 15/00 |

OTHER PUBLICATIONS

International Search Report for PCT/IB2023/052727, dated Dec. 11, 2023.

Meng, "Personalized Perception and Interaction with Medical Information in Mixed Reality Environments," Technische Universität München, 136 pages Nov. 3, 2016.

Canadian Office Action received for CA3147594 dated Jan. 2, 2025, 5 pages.

\* cited by examiner

SYSTEMS AND METHODS FOR DISPLAYING LAYERED AUGMENTED ANATOMICAL FEATURES

CROSS REFERENCE TO RELATED APPLICATIONS

This U.S. patent application claims priority under 35 U.S.C. § 119(e) to U.S. Provisional Application 63/317,423, filed on Mar. 7, 2023. The disclosure of this prior application is considered part of the disclosure of this application and is hereby incorporated by reference in its entirety.

TECHNICAL FIELD

This disclosure relates generally to a method, system and user device for displaying anatomical features and, more particularly, one or more layers of anatomical features.

BACKGROUND

This section provides background information related to the present disclosure and is not necessarily prior art.

Augmented reality technology has the ability to alter, or augment, a user's view of the surrounding environment by overlaying computer-generated images onto the user's view of the real world, creating a composite view consisting of both real and virtual elements. Augmented reality offers the user an enriching experience by augmenting, via overlaid digital content, the user's perception of their environment and their immediate surroundings. The user may augment their view through various electronic devices, such as wearable technology (e.g., headsets, glasses, smart watches, etc.), tablets, laptops, mobile devices, or other devices. The user can use these electronic devices to augment their perception of their environment by overlaying, for instance, information about their surroundings, or graphical images to enhance their perception of their current environment.

Augmented reality can be used in a variety of environments by a variety of users to educate each user about their surroundings. For example, a railyard worker can wear augmented reality glasses that allow them to view information about trains in the railyard, or a biologist may use augmented reality to identify different species of plants surrounding them.

Healthcare professionals, such as doctors and nurses, are in continuous need of technological assistance in order to treat their patients. Particularly, healthcare professionals constantly need to obtain and accumulate data on their patients in order to assess the best treatment plan for the patient. Healthcare professionals would greatly benefit from using augmented reality to gather data on their patients. While known augmented reality technology has been used for healthcare professionals to gather patient data, a continuous need for improvement remains in the pertinent art.

SUMMARY

This section provides a general summary of the disclosure, and is not a comprehensive disclosure of its full scope or all of its features.

One aspect of the disclosure provides a method for displaying a target individual. The method includes receiving, at a processor, a plurality of reference markers that characterize a target individual. The method also includes selecting a first reference image file and a second reference image file from a database of reference image files. The method further includes displaying, on a display, a first graphical representation of the first reference image file and a second graphical representation over a visual representation of the target individual. The first reference image file is associated with a first anatomical layer and the second reference image file is associated with a second anatomical layer that is different than the first anatomical layer. The method additionally includes modifying, by the processor, at least one of (i) the first graphical representation or (ii) at least one of the plurality of reference markers. The method also includes displaying, on the display, a modified visual representation of the target individual based on the modified at least one of (i) the first graphical representation or (ii) the at least one of the plurality of reference markers.

In some examples, the method further includes modifying, by the processor, the first reference image file based on the plurality of reference markers. In these examples, displaying, on the display, the first graphical representation of the first reference image file over the visual representation of the target individual includes displaying the modified first reference image. In some implementations, the method also includes modifying, by the processor, the second graphical representation of the second reference image file and updating, on the display, the modified visual representation of the target individual based on the modified second graphical representation of the second reference image file.

In some configurations, the method additionally includes displaying, on the display, the first graphical representation of the first reference image file over the first graphical representation of the second reference image file. In these configurations, displaying the first graphical representation of the first reference image file over the second graphical representation of the second reference image file may further include determining that the first anatomical layer associated with the first reference image file is closer to an outer anatomical layer than the second anatomical layer associated with the second reference image file.

Another aspect of the disclosure provides a system for displaying a target individual. The system includes a display, data processing hardware in communication with the display, and memory hardware in communication with the data processing hardware. The memory hardware stores instructions that, when executed on the data processing hardware, cause the data processing hardware to perform the following operations. The operations include receiving a plurality of reference markers that characterize a target individual. The operations also include selecting a first reference image file and a second reference image file from a database of reference image files. The operations further include displaying, on the display, a first graphical representation of the first reference image file and a second graphical representation over a visual representation of the target individual. The first reference image file is associated with a first anatomical layer and the second reference image file is associated with a second anatomical layer that is different than the first anatomical layer. The operations additionally include modifying at least one of (i) the first graphical representation or (ii) at least one of the plurality of reference markers. The operations also include displaying, on the display, a modified visual representation of the target individual based on the modified at least one of (i) the first graphical representation or (ii) the at least one of the plurality of reference markers.

In some examples, the operations further include modifying the first reference image file based on the plurality of reference markers. In these examples, displaying, on the display, the first graphical representation of the first reference image file over the visual representation of the target individual includes displaying the modified first reference image. In some implementations, the operations also include modifying the second graphical representation of the second reference image file and updating, on the display, the modified visual representation of the target individual based on the modified second graphical representation of the second reference image file.

In some configurations, the operations additionally includes displaying, on the display, the first graphical representation of the first reference image file over the first graphical representation of the second reference image file. In these configurations, displaying the first graphical representation of the first reference image file over the second graphical representation of the second reference image file may further include determining that the first anatomical layer associated with the first reference image file is closer to an outer anatomical layer than the second anatomical layer associated with the second reference image file.

Optionally, either the system or the method may include the following features. The first reference image file may correspond to at least one inner anatomical feature. The at least one inner anatomical feature may include a bone, an organ, or fat. Selecting the first reference image file and the second reference image file from the database of reference image files may include determining a relationship among the plurality of reference markers and identifying that, from among the reference image files, at least one of the first reference image file or the second reference image file most closely matches the relationship. In some examples, each of the first graphical representation of the first reference image file and the second graphical representation of the second reference image file are selectably removable and selectively insertable by a user while viewing the modified visual representation of the target individual on the display.

The details of one or more implementations of the disclosure are set forth in the accompanying drawings and the description below. Other aspects, features, and advantages will be apparent from the description and drawings, and from the claims.

DESCRIPTION OF DRAWINGS

The drawings described herein are for illustrative purposes only of selected configurations and not all possible implementations, and are not intended to limit the scope of the present disclosure.

Like reference symbols in the various drawings indicate like elements.

DETAILED DESCRIPTION

Figure 1A:
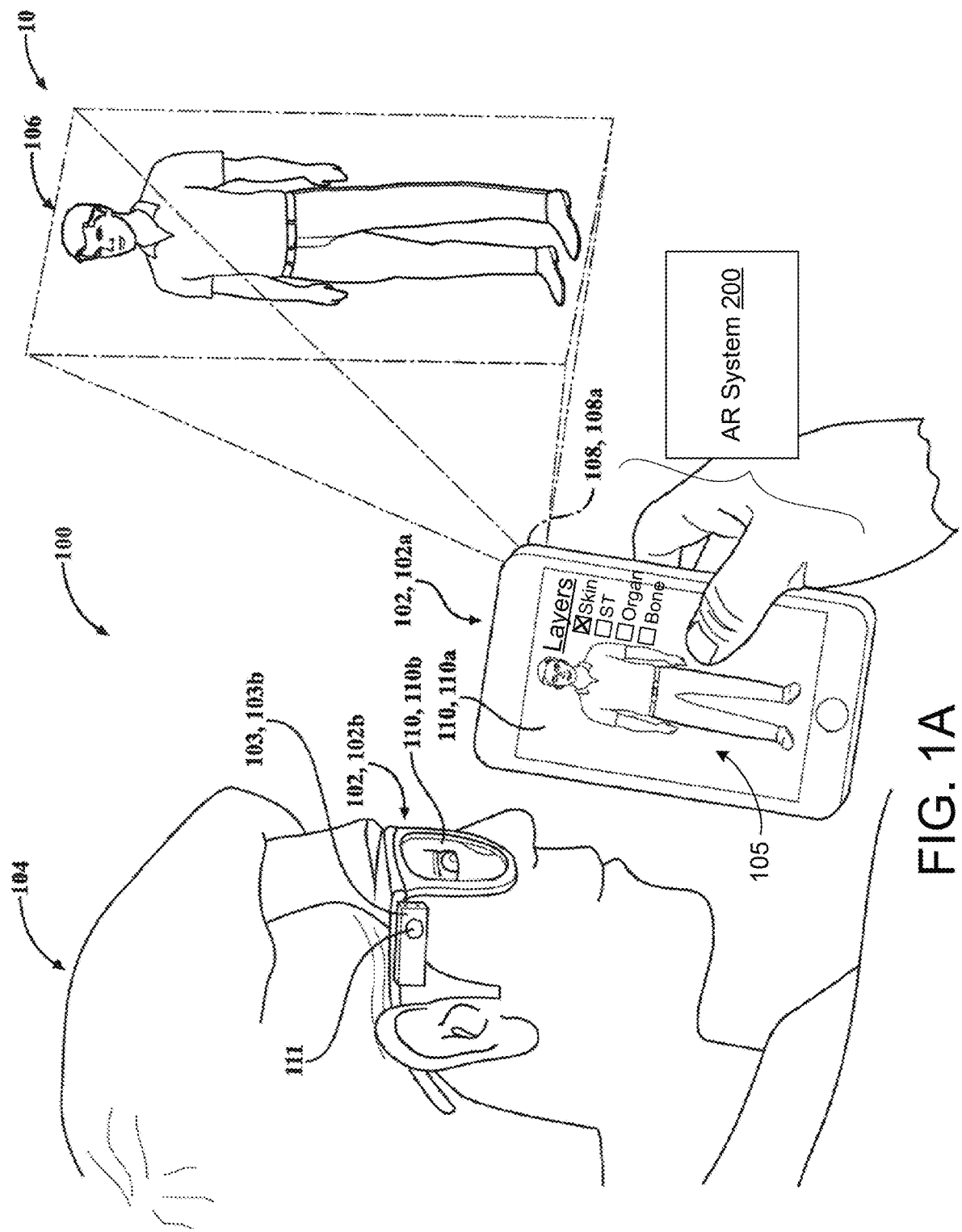
FIGS. 1A and 1B are schematic views of example augmented reality environments in accordance with the principles of the present disclosure.

Some of the implementations of the disclosure will be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Example implementations provide methods, user devices, and systems for displaying augmented anatomical features. An augmented reality (AR) device, such as an AR headset or other electronic device (e.g., a phone, a tablet computing device, or other computer), may be used to overlay computer-generated or virtual images onto a real world view. Particularly, a healthcare professional, such as a doctor or nurse, may use an AR device to view virtual images of anatomical features of a human body overlaid on a target individual, such as a patient, when the target individual is in view of the healthcare professional. The AR device may project the virtual images onto a display of the AR device such that the virtual images of anatomical features approximate one or more characteristics (e.g., size, location, shape, etc.) of the target individual's actual anatomical features. For example, the AR device may project the virtual images onto a display of the AR device such that the virtual images are located over an approximated appropriate location of the target individual's actual anatomical features according to the anatomy of the target individual. The virtual images may assist a healthcare professional in more accurately assessing a treatment plan or otherwise treating the patient by enhancing the health care professional's visualization of the patient's body.

In at least one aspect, the AR device includes a software application configured to identify a plurality of reference markers on the image of the patient and to determine an anatomical profile of the target individual based on the plurality of reference markers where the anatomical profile includes a plurality of inner anatomical features. The software application is further configured to display, on the display, a graphical representation of the inner anatomical features onto the visual representation of the body so as to assist in the identification of the inner anatomical features.

In another aspect, software application includes a list of medical procedures to choose from. The software application may have access to a database populated with a plurality of future state anatomical profiles corresponding to the selected medical procedure, wherein a graphical representation of the future state anatomical profile is overlaid on the image of the patient and modifies the inner anatomical features based on the selected medical procedure. Accordingly, the image capture device displays how the selected medical procedure affects the inner anatomical features of the patient.

In another aspect, the image capture device is configured to map the patient so as to generate an initial three-dimensional representation of the body. The software application may have access to a database that is populated with a plurality of preferred anatomical profiles which correspond to a plurality of reference markers on the initial three-dimensional representation of the patient. The preferred anatomical profile is a profile of a person having a preferred body type. The software application overlays in three dimensions the anatomical features based on the selected medical procedure with the preferred anatomical profile and displays a graphical representation of the preferred three-dimensional representation of the body overlaid on the initial three-dimensional representation of the body. Accordingly, the patient can see what he or she would look like having a preferred body type. As this body is mapped and generated in three-dimensions, the patient can observe the preferred body type in three-dimensions.

The AR device may also have capabilities to design a future state for the target individual. That is, not only can the software application associated with the AR device select a medical procedure with a corresponding future state anatomical profile, but the software application is also capable of allowing the user (e.g., the healthcare professional) to configure (e.g., manually configure) the future state of a target individual. For instance, many different medical procedures occur at a particular local site of the human body, but may impact portions of the human body beyond the particular local site. As an example, removing fatty tissue or a mass of cell growth may not only alter a soft tissue region of the body near the site of the removed fatty tissue or mass, but also impact a musculoskeletal layer and/or a skin layer for the patient. For instance, portions of a patient's body (e.g., certain anatomical features) may undergo atrophy, hypertrophy, or hyperplasia due to disease or other conditions of the patient. When a medical procedure occurs, the state of the patient's body (e.g., the atrophy, hypertrophy, or hyperplasia) may change and result in changes to anatomical features that are parts of different systems of the human body. That is, since the body is an organism of interconnected systems, a change or modification to a particular portion of the human body may inevitably cause some modification to other portions (e.g., other systems) of the human body.

The AR device and its corresponding systems include functionality that is capable of representing the impact of changes to the human body (i.e., predict a future physical state and represent that state graphically). To represent these changes, the visualization of the target individual may be associated with a plurality of anatomical layers. For instance, the visualization of the target individual being displayed to the user can be a collection of reference images overlain on a visual representation of the target individual. Here, the reference images graphically represent one or more anatomical features and can each be associated with one or more anatomical layers. For instance, a reference image may depict multiple anatomical features and all of these anatomical features depicted correspond to a single layer and/or each anatomical feature includes its own anatomical layer designation.

By having these anatomical layer associations, the user may be able to toggle on or off a particular anatomical layer to portray the visualization of the target individual in a customizable manner. For instance, the healthcare professional uses the visualization to explain a procedure to a patient or to design a particular procedure. In the case of a plastic surgeon, the plastic surgeon can show a patient that removing fatty tissue in a tummy tuck will have an effect on the patient's body beyond the local site of the fatty tissue. In this example, the plastic surgeon can toggle on a soft tissue layer that results in a graphical representation of the soft tissue layer of the patient (e.g., a modified virtual image overlain on the virtual representation of the patient to approximate the actual soft tissue of the patient). With the soft tissue layer depicted, the plastic surgeon can modify one or more reference markers on the graphical representation of the soft tissue layer to indicate the removal of the fatty tissue of the patient. In response to these modifications input by the plastic surgeon (e.g., changes to one or more reference markers), the system can determine whether these modifications impact other anatomical features associated with other layers of the visualization of the patient. That is, the surgeon makes changes to a particular active layer and the changes to the active layer are carried through to other non-active layers and/or other active layers. In this respect, after inputting the modifications to the active layer (e.g., a particular soft tissue layer with the fatty tissue to be removed), the surgeon may toggle off or on layers to illustrate to the patient the predicted effects to the body of the patient.

In addition to being a helpful communication tool between the patient and provider (e.g., the healthcare professional), the system may also enable the healthcare professional to understand how changes he or she may make to a particular local site (e.g., the fatty tissue) will potentially impact other portions of the patient's body. For instance, the healthcare provider designs a procedure that removes a certain portion of soft tissue, but fails to realize that the particular design may cause a potential unintended consequence on the skeletal system of the patient (e.g., results in weakening a muscle sheath associated with a particular bone). By visualizing these changes across all impacted layers, the system is capable of producing a predicted physical future state for anatomical features beyond the directly modified local site. In some examples, the system is configured to represent the changes that automatically occur to other layers and/or to other anatomical features by representing these computer-automated changes in a particular color. For instance, the site of the user-input changes is rendered in red in the virtualization of the target individual and the computer-automated changes predicted to occur based on the user-input changes are rendered in orange in the visualization of the target individual.

Figure 1B:
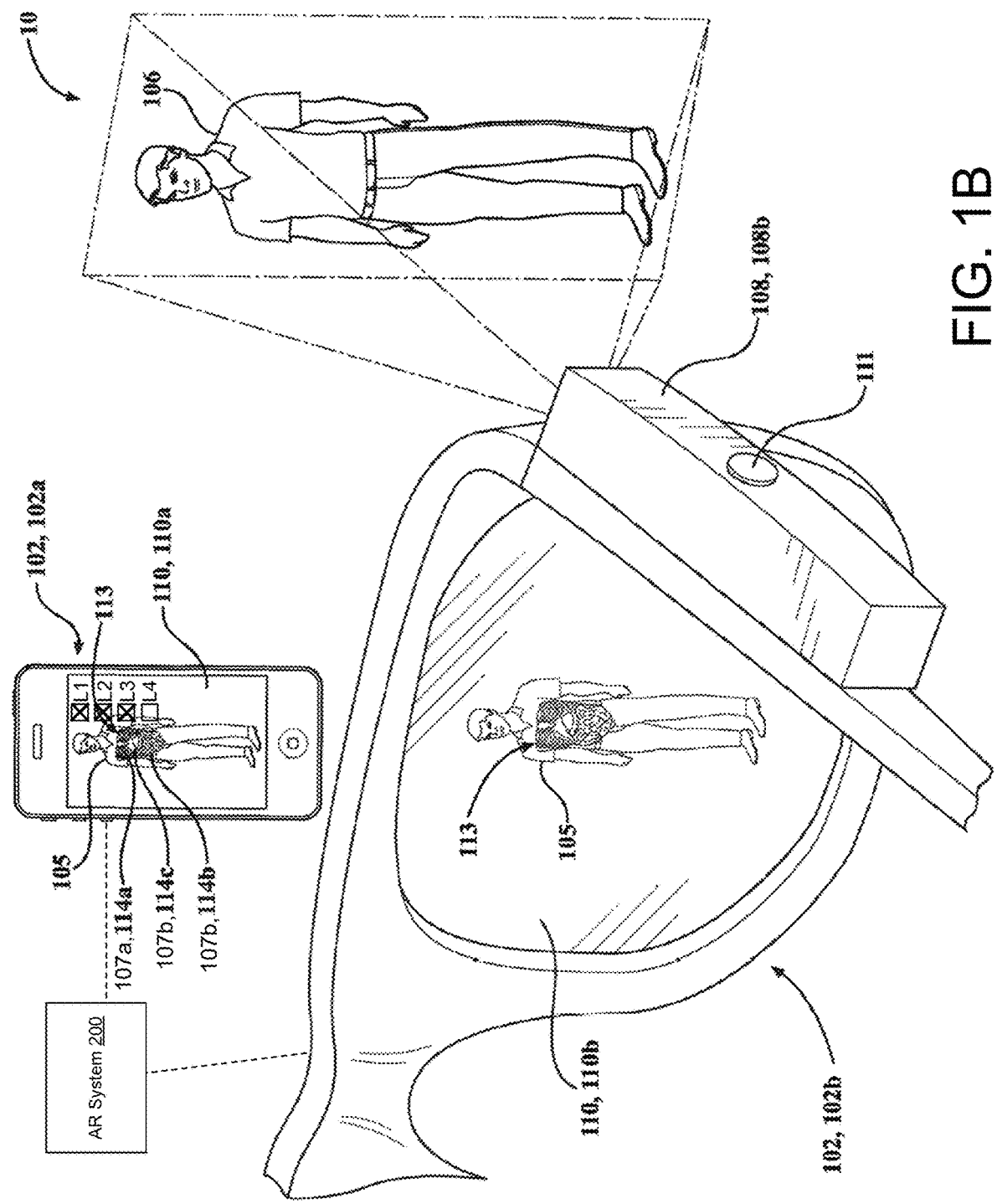

Referring now to FIGS. 1A and 1B, an AR environment 100 generally includes an AR device 102 being used by a user 104 to visualize a target individual 106. The AR device 102 uses an AR system 200 to display augmented anatomical features corresponding to the target individual 106. As will be described in more detail below, the user 104 may use the AR device 102 (e.g., a first or a second AR device 102, 102a-b) in an AR environment 100 (e.g., a healthcare environment) to enhance the user's view of the target individual 106. For example, the user 104 may be a doctor, the target individual 106 may be a patient, and the AR environment 100 may be a doctor's office, such that the doctor is able to examine the patient in the doctor's office. In another example, the user 104 may be a paramedic providing emergency treatment to a target individual 106 in an environment 100 of an ambulance. While the user 104 is generally shown and described herein as being a healthcare professional (e.g., a doctor, nurse, physical therapist or trainer, paramedic, medical assistant, pharmacist, etc.), and the target individual 106 is generally illustrated and described herein as being a healthcare patient, the user 104 or target individual 106 may include various other persons within the scope of the present disclosure. For example, the individual 106 may be an athlete, student, or other individual that has a body and is subject to examination or study by another user 104. In this regard, the AR device 102 may be used in a wide range of settings by a variety of users 104 to examine a target individual 106 in a variety of environments.

The AR device 102 may include an image capture device 108 and a display 110. As will be described in more detail below, during use, the image capture device 108 may obtain data about the environment 100 and, particularly, the target individual 106 located in the environment 100. With data regarding the target individual 106, the display 110 may display, for user 104 to view, a composite view of the environment 100 overlaid with virtual images (e.g., generated by the AR device 102 and/or accessible to the AR device 102). The AR device 102 may be any computing device that is capable of executing with the functionality of the AR system 200. In this regard, the AR device may include data processing hardware and memory hardware executing instructions that cause the data processing hardware to perform the various operations of the AR system 200. Some examples of the AR device 102 include a smartphone, tablet computer, smart watch, smart speaker, smart glasses (e.g., an AR headset), or other suitable mobile computing device.

In some implementations, such as FIGS. 1A and 1*i*, the environment 100 includes a first AR device 102*a* and a second AR device 102*b*. Here, the first AR device 102*a* is a mobile computing device (e.g., a smartphone or mobile computer) and the second AR device 102*b* is an AR headset. References herein to the AR device 102 will be understood to apply equally to the first AR device 102*a* and/or the second AR device 102*b*.

The first AR device 102*a* may include an image capture device 108*a* (e.g., a camera) and a display 110*a* (e.g., a screen). During use, the image capture device 108*a* may capture images of the environment 100 and, particularly, the target individual 106. The display 110*a* of the first AR device 102*a* may be used to display a composite view of the environment 100, captured by the camera 108*a*, and overlaid with virtual images (e.g., by the AR system 200 using the AR device 102*a*). The first AR device 102*a* may include a keyboard, mouse, microphone, camera 108*a*, or touchscreen for allowing user 104 to input data to the first and/or second AR device 102*a*, 102*b*.

The second AR device 102*b* may include an image capture device 108*b* (e.g., a camera) and a display 110*b* (e.g., an eyepiece lens). During use, the image capture device 108*b* may capture images of the environment 100 and, particularly, the target individual 106. The display 110*b* may display a composite view of the environment 100, captured by camera 108*b* and/or the camera 108*a*, and overlaid with virtual images (e.g., from the AR system 200 using the AR device 102*b*). The second AR device 102*b* may include a trackpad 111, camera 108*b*, microphone, eye tracking device, or gesture tracking device for allowing user 104 to input data to the first and/or second AR device 102*a*, 102*b*. For example, the user 104 may input data and otherwise interact with the second AR device 102*b* by touch via trackpad 111; spoken commands via a microphone; eye gestures via the camera 108*b*; positional tracking of hands or other body parts via the camera 108*b*; hand gesture tracking via the camera 108*b*; or positional tracking of objects such as wands, styluses, pointers, or gloves via the camera 108*b*.

Though the examples shown depict the AR device 102 as a first AR device 102*a* or a second AR device 102*b*, it should be noted that AR device 102 may be any device (e.g., AR glasses, AR helmet, tablet, etc.) capable of overlaying computer-generated or virtual images (e.g., graphical representation 113, including the virtual images 114*a-c*) onto a real word view (e.g., visual representation 105).

The AR device 102 operating in conjunction with the AR system 200 is configured to generate a visual representation 105 of the target individual 106. That is, the image capture device 108 of the AR device 102 may capture image data (e.g., via a vision sensor such as a camera) that can be projected onto the display 110 to represent the actual body of the target individual 106. This visual representation 105 may be the result of one or more two-dimensional (2D) images capturing the target individual 106 or a visualization of point cloud data captured using one or more cameras associated with the image capture device 108 of the AR device 102. In this respect, the visual representation 105 may be either a 2D representation of the target individual 106 or a 3D representation of the target individual 106 such that the visual representation 105 displayed on the display 110 is rotatable to other viewing angles to represent a 3D model of the target individual 106.

As shown in FIG. 1A, the first AR device 102*a* includes a display 110*a* that depicts the visual representation 105 of the target individual 106. For instance, an application executing the AR system 200 on the AR device 102 renders the visual representation 105 in a viewing window within the display 110*a*. Here, the application includes a layer menu along with the visual representation 105 that indicates one or more anatomical layers 107 associated with the visual representation 105. An anatomical layer 107 refers to one or more anatomical features that have been associated with each other to define a layer. Although the anatomical layers 107 may be completely customizable, in some examples, each anatomical layer 107 may correspond to a human body system, subsystem, or some other body-related categorization. For example, the systems of the body are generally the integumentary system, the skeletal system, the muscular system, the nervous system, the endocrine system, the cardiovascular system, the lymphatic system, the digestive system, the urinary system, and the reproductive system. In this respect, a subsystem may correspond to parts of a particular system. For instance, the integumentary system is broken down into three subsystems: a skin layer, a subcutaneous layer, and a dermatomes layer.

FIG. 1A illustrates that each layer 107 may be selectively toggled on or off by the user 104. That is, one or more graphical representations corresponding to a layer may be selectively insertable (toggled on) or removable (toggled off) from the visualization of the target individual 106. For instance, in FIG. 1A, an organ layer, a bone layer, and a soft tissue layer are toggled off while a surface layer is togged on (e.g., indicated by an "X") to depict the clothed target individual 106. In contrast, FIG. 1B illustrates the bone layer (e.g., showing the rib cage of the target individual 106), the organ layer, and the surface layer toggled on while the soft tissue layer is toggled off.

Referring now to FIG. 1B, the AR devices 102*a*, 102*b* may display a graphical representation 113 for the target individual 106 or portion thereof. In some implementations, the graphical representation 113 is considered an augmented reality of the target individual 106 because instead of representing the actual anatomical features of the target individual 106, the graphical representation 113 is a virtual approximation of the target individual's anatomical features constructed from virtual images 114 (i.e., reference images). In some examples, the virtual images 114 used to form the graphical representation 113 may be stitched together from one or more actual images of anatomical features of the target individual 106 if such images exist or have been collected with other medical imaging devices and are accessible to the AR device 102 and/or AR system 200. Alternatively, the graphical representation 113 may be a hybrid of actual images of anatomical features of the target individual 106 and reference images that do not correspond to actual anatomical features of the target individual 106.

In some implementations, the AR device 102 may display the graphical representation 113 even when the target individual 106 is fully clothed. This is advantageous as it saves time because the target individual 106 does not have to remove their clothing. The graphical representation 113 for the target individual 106 may include one or more virtual images 114 of anatomical features. For example, FIG. 1B illustrates that three virtual images 114a-114c that correspond to virtual images 114 of internal (e.g., bones or other organs) or external (e.g., skin or contours thereof) anatomical features. In some implementations, the AR device 102 uses 3D data corresponding of the target individual 106 to generate the graphical representations 113. As will be explained in more detail below, in some implementations, the graphical representation 113 includes virtual images 114 of a detailed underlying anatomy of the target individual 106.

As illustrated in FIG. 1B, the second AR device 102b may display the graphical representation 113 on the eyepiece display 110b, and the first AR device 102a may display the graphical representation 113 on the display 110a. As previously described, the graphical representation 113 displayed on display 110 and overlaid on top of visual representation 105 of the target individual 106 may include computer-generated virtual images (e.g., the virtual images 114a-c of the anatomical features). In the example shown, AR device 102 displays, on the display 110, the graphical representation 113 including virtual images 114a-114c where each virtual image 114 represents an organ, bone, or structure in the human body.

A first virtual image 114a represents a ribcage of the human body and may be assigned to or associated with a bone layer 107a as its designated anatomical layer 107. Virtual image 114a is overlaid on the visual representation 105 of the target individual 106 at a location approximating where the ribcage of the target individual 106 is located. A second virtual image 114b represents intestines of the human body and may be assigned to or associated with an organ layer 107b as its designated anatomical layer 107. Virtual image 114b is overlaid on the visual representation 105 of the target individual 106 at a location approximating where the intestines of the target individual 106 are located. A third virtual image 114c represents a pancreas of the human body and may also be assigned to or associated with the organ layer 107b as its designated anatomical layer 107. Virtual image 114c is overlaid on the visual representation 105 of the target individual 106 at a location approximating where the pancreas of the target individual 106 is located. Virtual images 114a-114c do not represent an exhaustive list of all virtual images 114, but rather an exemplary list of virtual images 114 that may be displayed by the AR device 102 in the graphical representation 113. Furthermore, the AR device 102 may display other virtual images 114 in addition to the virtual images 114a-114c, or may omit one or more virtual images 114a-114c, without departing from the teachings herein.

The graphical representation 113, in combination with the visual representation 105, enhances the view and experience of the user 104 by creating a composite view of both real and virtual images 114 on the display 110. The user 104 may view, through the display 110, the visual representation 105 of the target individual 106 with the virtual images 114a-114c of organs and other anatomical features represented by the graphical representation 113 of the target individual 106. The anatomical features may include organs, bones, muscles, blood vessels, tendons, ligaments, or nerves. In some implementations, the virtual images 114a-114c are not actual images of the internal organs, bones, or other bodily structures of target individual 106, but rather are representative depictions (e.g., illustrations) of those bodily structures. This allows the AR device 102 to store representative virtual images 114a-114c that can be used for any target individual 106. Furthermore, in some situations, it may be advantageous to use representative virtual images 114 that are modifiable by the AR system 200 to simulate the anatomical features of the target individual 106 because the AR system 200 is more lightweight and less computationally expensive (e.g., requires less storage) than if the functionality of the AR system 200 required personalized images for each target individual for the visualization. By being lightweight, the AR system 200 may be capable of being deployed in lightweight environments that have a finite amount of computing resources (e.g., a mobile phone or a headset) to dedicate to its processes. That is, certain computing devices consume a greater portion of their total resources with general operating functionality and do not have significant amounts of excess computing resources to dedicate to specialized computing processes like visualization of a target individual 106.

As shown in FIGS. 1A and 1, the AR device 102 is capable of displaying visual data on a display 110 to generate the visual representation 105 and/or the graphical representation 113 of the target individual 106. For instance, the first AR device 102a is shown displaying visual data on the display 110a and, similarly, the second AR device 102b is capable of displaying visual data on the eyepiece display 110b. The AR device 102 may detect the target individual 106 by using image capture device 108. AR device 102 may then display, on the display 110, the visual representation 105 of a body of the target individual 106. In some implementations, the visual representation 105 is a live or current (e.g., real time) image of the target individual 106. In other implementations, the visual representation 105 is a still image (e.g., a photograph) of the target individual 106. In some implementations, the image capture device 108 includes an infrared camera that uses infrared laser scatter beam technology, for example, to create a three-dimensional visual representation 105 of the target individual 106.

Figure 6:
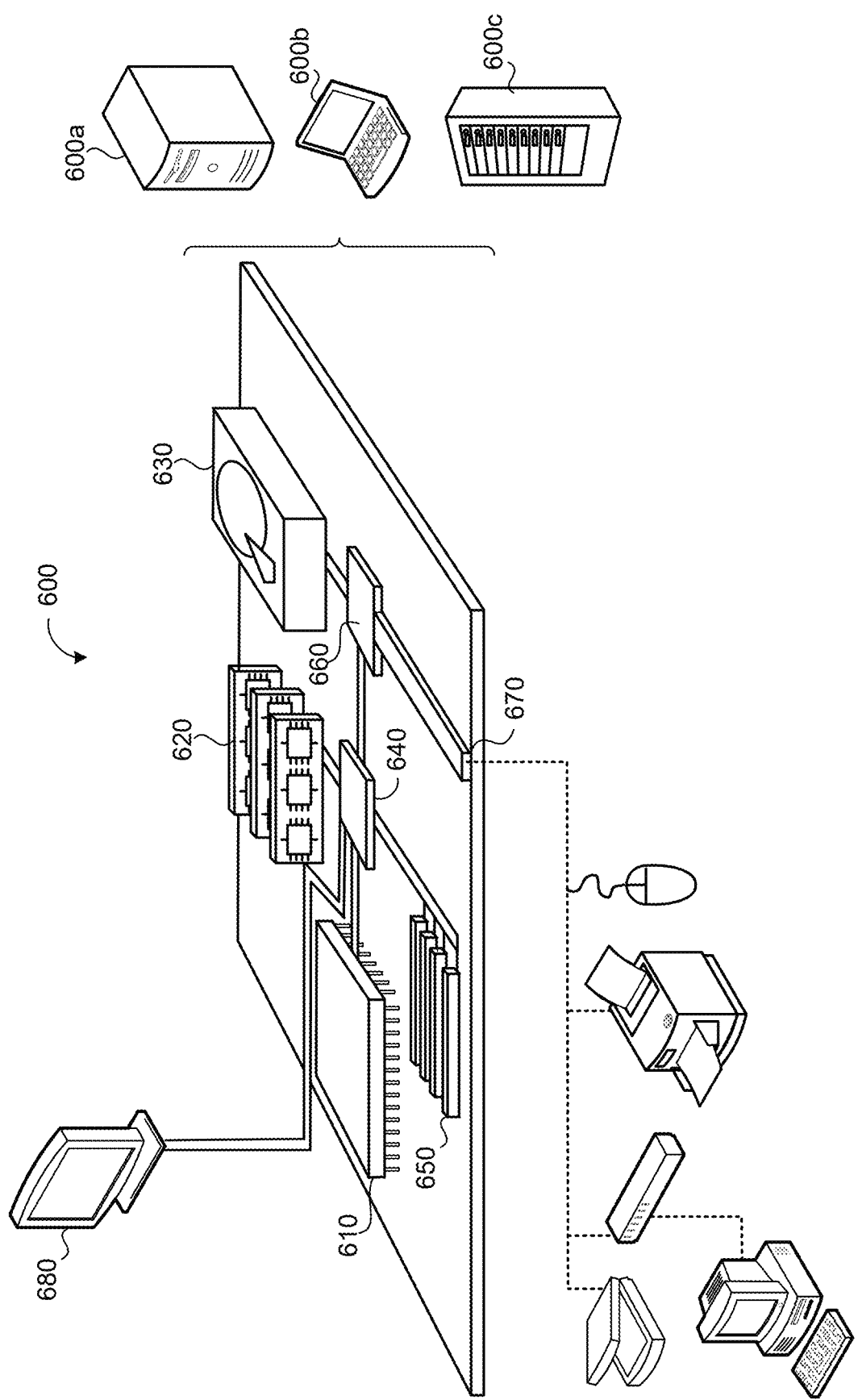
FIG. 6 is a schematic view of an example electronic device executing instructions for displaying augmented anatomical features in accordance with the principles of the present disclosure.

In some implementations, the AR device 102 may use the image capture device 108 to take a still picture or record a video of the target individual 106. In this regard, the visual representation 105 of the target individual 106 may include a still picture or a recorded video. The AR device 102 may then overlay virtual images 114 of anatomical features onto the still picture or recorded video of target individual 106. The AR device 102 may then display the still picture or recorded video with the overlaid virtual images 114 onto the display 110. This may be advantageous, particularly for educational purposes, as it assists a healthcare professional in educating a patient about their own anatomy by showing the patient how their own individual anatomy approximately works. In other implementations, the AR device 102 may be able to take a picture or record a video of the target individual 106 with the visual representation 105 that includes the virtual images 114 of organs and other anatomical features. The AR device 102 may store the picture or recorded video in a storage resource, such as the storage device 630 (FIG. 6).

Figure 2:
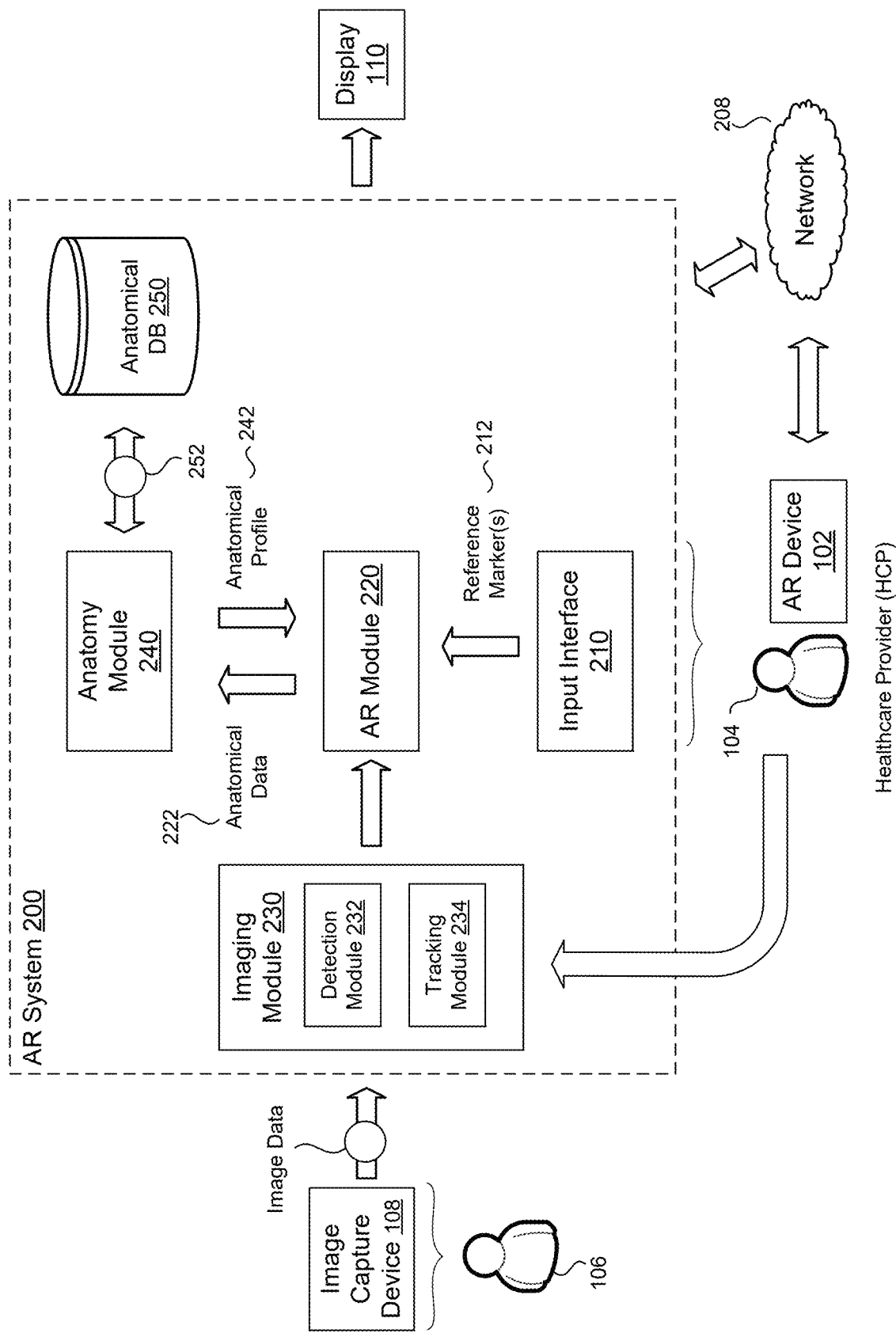
FIG. 2 is a schematic view of an example augmented reality system for the augmented reality environment of FIGS. 1A and 1B.

With reference to FIG. 2, the AR system 200 is configured to display or to facilitate the display of augmented anatomical features (e.g., virtual images 114a-114c of FIG. 1). The AR system 200 may be deployed on the AR device 102 (e.g., as an application) or in communication with the AR device 102. Generally speaking, the AR system 200 includes an input interface 210, an AR module 220, an imaging module 230, an anatomy module 240, and an anatomical database 250. The imaging module 230 is configured to be in communication with at least one image capture device 108 in order to receive image data corresponding to the target individual 106. In some implementations, such as FIG. 2, the imaging module 230 includes a detection module 232 and a tracking module 234.

Although FIG. 2 depicts these components of the AR system 200 residing together (e.g., together on the AR device 102), in some configurations, some or all of these components of the AR system 200 reside in a location that is remote from the AR device 102. For example, one or more components of the AR system 200 reside remotely and in communication with the AR device 102 through a wired or wireless communication network 208 (e.g., WiFi, Bluetooth, etc.). In particular, the AR system 200 may include and/or otherwise communicate through a wired or wireless network 208 that provides access to the AR device 102 and that provides for the performance of services on remote devices. Accordingly, the network 208 may allow for interaction between the user 104 using the AR device 102 and the AR system 200. For instance, the network 208 may provide the user 104 access to the AR system 200 in order for the AR system 200 to receive event data input by the user 104 (e.g., input by an interaction with the AR device 102). In turn, AR system 200 may store event data in a storage resource (e.g., memory) on the AR device 102 or accessible via the network 208 (e.g., a server in communication with the network 208).

As will be described in more detail below, the AR system 200 may provide a user 104 (e.g., a healthcare provider) with the ability to enhance the user's 104 view of a target individual 106. In this regard, the AR device 102 may include data processing hardware (e.g., a computing device that executes instructions), memory hardware, and the display 110 in communication with the data processing hardware and/or memory hardware.

The input interface 210 may provide the user 104 access to, and the ability to interact with, the AR module 220 through the AR device 102. In some examples, the input interface 210 is able to receive input from a keyboard, touchpad, mouse, microphones, eye-tracking device, gesture tracking device, and/or a camera in order to enable the user 104 to input data to the AR system 200. In some examples, in addition to, or in lieu of, the display 110, the AR device 102 may include one or more speakers to output audio data to the user 104.

In some implementations, the user 104 interacts with the input interface 210 by inputting data corresponding to reference markers 212. The reference markers 212 may correspond to locations on the target individual 106. For example, the reference markers 212 may be designated by the user 104 to indicate a reference location on a 2D or 3D projection of the target individual 106 (e.g., the visual representation 105 of the target individual 106). As an example, the user 104 may identify a particular pixel or pixel area in an image (e.g., by tapping, touching, or somehow selecting) to place a reference marker 212 at a virtual location in the image that corresponds to an anatomical location on the target individual 106. That is, if the user 104 selects a pixel at the location where the image depicts the tenth rib of the target individual 106, the AR system is configured to place a reference marker 212 on the target individual 106 at tenth rib.

Data corresponding to the reference markers 212 may be sent to the AR module 220. The AR module 220 may communicate with the anatomy module 240. For instance, the AR module 220 may send anatomical data 222 corresponding to the reference markers 212 to the anatomy module 240. The AR module 220 may then request data (e.g., reference image files 252) corresponding to graphical representations (e.g., virtual images 114) of anatomical features from the anatomy module 240. The anatomy module 240 may then retrieve data (e.g., reference image files 252) corresponding to the graphical representations 113 of anatomical features, a future state anatomical profile, or a preferred anatomical profile from the database 250. The anatomy module 240 may then generate an anatomical profile 242, including graphical representations of anatomical features (e.g., virtual images 114), to be displayed on the display 110.

As an example, the database 250 may be populated with a discrete number of reference image files 252. Each reference image file 252 may correspond to one or more characteristics (e.g., age, height, weight, gender, race, shape, etc.) of an individual (e.g., target individual 106). In such an aspect, the AR device 102 may process the reference markers 212 and/or other data inputted into the input interface 210, to automatically select a reference image file 252 that best matches the characteristics (e.g., location, spacing, etc.) of the reference markers 212 and/or other data input into the input interface 210. In other implementations, the user 104 may select a reference image file 252 that best matches the reference markers 212 and/or other data input into the input interface 210. For instance, the target individual 106 may be a male adult that is 5'11". The database 250 may be populated with reference image files 252 corresponding to a male adult that is 5'8" and other reference image files 252 corresponding to a male adult that is 6'2". The AR system 200 may select the reference image file 252 of the adult male that is 6'2" in cases where the anatomical profile of the adult male that is 6'2" matches the reference markers 212 more closely than the anatomical profile of the adult male that is 5'8". For example, the anatomical features of the reference markers 212 projected on the anatomical profile of the adult male that is 6'2" more closely align (e.g., by distance) with the actual anatomical features of the 6'2" adult male than the anatomical features of the reference markers 212 projected on the anatomical profile of the adult male that is 5'8".

The AR system 200 (e.g., at the AR module 220) may scale the inner anatomical features of the selected reference image file 252 so as to fit within a visual representation (e.g., visual representation 105) of the body of the target individual 106. Using the same example, the AR module 220 may shrink the inner anatomical features of the selected reference image file 252 so as to fit within the smaller visual representation of the target individual 106 and transform a graphical representation 113 corresponding to the selected reference image file 252 to a modified graphical representation 113. For instance, a scale factor is derived from the difference (e.g., the distance) between the reference markers 212 and the anatomical features that the reference markers 212 refer to in the anatomical profile of the reference image file 252.

In some implementations, the AR system 200 performs a look up in the database 250 with data corresponding to the reference markers 212. The AR system 200 may use the data corresponding to reference markers 212, and in some implementations the plurality of target data, to determine data corresponding to the anatomical features' characteristics (e.g., size, location, etc.) prior to selecting the reference image file 252. For example, the AR system 200 may use the reference markers 212 and data captured from the image capture device 108 (e.g., an image capture device 108 using infrared laser scatter beam technology) to create a graphical representation (e.g., graphical representation 113, including the virtual images 114) of one or more anatomical features of the target individual 106. In particular, the AR system 200 may transmit the data corresponding to the anatomical features' characteristics to a processor (e.g., processor 610 of FIG. 6) and display the graphical representation 113, including any virtual images 114 of the anatomical features, on the display 110 at a location corresponding to the target individual 106 (see FIG. 1).

In some implementations, the AR system 200 searches the database 250 to find an anatomical profile corresponding to the reference markers 212. For example, the AR system 200 may use the distance between reference markers 212 to find an anatomical profile having similar distances between the reference markers 212. For example, if the patient is a male, that is 5'10" having the left and right shoulders that are spaced apart from each other 18 inches, the left and right hips that are spaced apart from each other 19 inches, the AR system 200 searches the database 250 to find reference image files 252 of a male that is 5'10 having reference markers 212 of similar spacing. It should be appreciated that the more reference markers 212 may be used to determine the corresponding anatomical profile other than just the left and right shoulders and the left and right hips. The graphical representation 113, including the virtual images 114, corresponding to the selected reference image files 252 are then displayed on the AR device 102 (e.g., as shown in FIGS. 1A and 1).

As will be explained in more detail below, in another aspect, the AR system 200 may be further configured to scale the graphical representation 113, including any relevant virtual images 114, based upon the characteristics of the target individual 106 relative to the reference image files 252. The AR system 200 may make a determination that the target individual 106 is larger or smaller than the selected reference image files 252. The AR system 200 may be further configured to increase or decrease the size of the inner anatomical features associated with the selected reference image files 252 so as to fit the reference markers 212 and/or other characteristics of the target individual 106. As an example, for a target individual 106 that is larger than the selected reference image files 252, the reference image files 252 may be enlarged. For instance, if the reference markers 212 indicate a shoulder spacing of 18 inches and the anatomical profile of the reference image file 252 has a shoulder spacing of 16.5 inches, the inner anatomical features may be scaled (e.g., enlarged) by a factor of 18/16.5=1.091.

The detection module 232 and tracking module 234 may obtain visual data corresponding to the target individual 106 and send it to the AR module 220. The visual data may be data corresponding to the current real world view of the image capture device 108 (i.e., a field of view of the image capture device 108). Furthermore, the visual data may include data such as the distance between the target individual 106 and the AR device 102, data characterizing whether the target individual 106 is in motion or at rest, or any other data that corresponds to the visualization of the target individual 106 by the AR device 102. The image capture device 108 may send data from the detection module 232 and the tracking module 234 to the AR module 220. The AR module 220 may use the data from the detection module 232 and the tracking module 234 corresponding to the image capture device's 108 real world view, coupled with virtual images 114 of the anatomical profile 216 to create a composite enhanced view (i.e., an AR view) of the target individual 106 on the display 110.

As previously mentioned, the AR module 220 of the AR system 200 is configured to modify a graphical representation 113 corresponding to a reference image file 252 based on information about the target individual 106. For example, the AR system 200 modifies the graphical representation 113 of a particular anatomical feature based on reference markers 212 associated with the visual representation 105 of the target individual 106 (e.g., based on dimensional comparisons between the reference markers 212 and the size of the particular anatomical feature depicted by the graphical representation 113). Here, because the final visualization of the target individual 106 may include multiple layers 107, the AR module 220 is configured to modify as many reference image files 252 as necessary to construct the multi-layer visualization of the target individual 107.

Additionally, the AR module 220 may apply the same modifying functionality to an already modified and graphically represented reference image file 252. That is, the user 104 may make changes to reference markers 212 to simulate a change to the body of the target individual 106. To enable this simulation, the AR module 220, based upon the reference marker changes, updates the graphical representation 113 for any affected layer 107 by modifying the graphical representation 113 to reflect the reference marker changes. Therefore, the AR module is able to constantly modify a graphical representation 113 (e.g., based on user inputs).

FIGS. 3A-3D are examples of the visualization of the target individual 106 rendered at the AR device 102. Here, the progression from FIG. 3A to FIG. 3D illustrates an example of how the user 104 may modify reference markers 212 causing the AR system 200 to update the visualization of the target individual 106 to account for the modifications. In some examples, to display the graphical representation 113, the AR system 200 identifies one or more reference markers 212 (e.g., based on received inputs at the AR device 102). For example, the user 104 designates pixel locations on the display 110 and the anatomical features at the pixel location is designated a reference marker 212. The AR system 200 may also determine the distance from each reference marker 212 to each of the other reference markers 212 and transmit data corresponding to the distances to a processor (e.g., processor 610 of FIG. 6). The AR system 200 may further perform a look up in a database (e.g., database 250 in FIG. 2) with data corresponding to reference markers 212 (e.g., memory 620 of FIG. 6). The AR device 102 may use the data corresponding to reference markers 212, and in some implementations the plurality of target data, to determine data corresponding to the anatomical features' characteristics (e.g., size, location, etc.). For example, the AR system 200 may use the reference markers 212 and the three-dimensional visual representation 105 of the target individual 106 created from image data captured by the image capture device 108 to create the graphical representation 113 (e.g., including the virtual images 114 of the anatomical features). In particular, the AR device 102 (e.g., via the AR system 200) may transmit the data corresponding to the anatomical features' characteristics to the processor (e.g., processor 610 of FIG. 6) and display the graphical representation 113, including the virtual images 114 of the anatomical features, on the display 110 at a location corresponding to the target individual 106 (see FIG. 1).

Referring now to FIGS. 3A-3D the AR device 102 may identify (e.g., assign) one or more reference markers 212 on the visual representation 105 (or a graphical representation 113 overlaid on the visual representation 105). As described above, in some implementations, the reference markers 212 are identified on a 3D visual representation 105 created using infrared laser scatter beam technology. Each reference marker 212 may correspond to a particular part of, or location on, the body of the target individual 106.

Figure 3A:
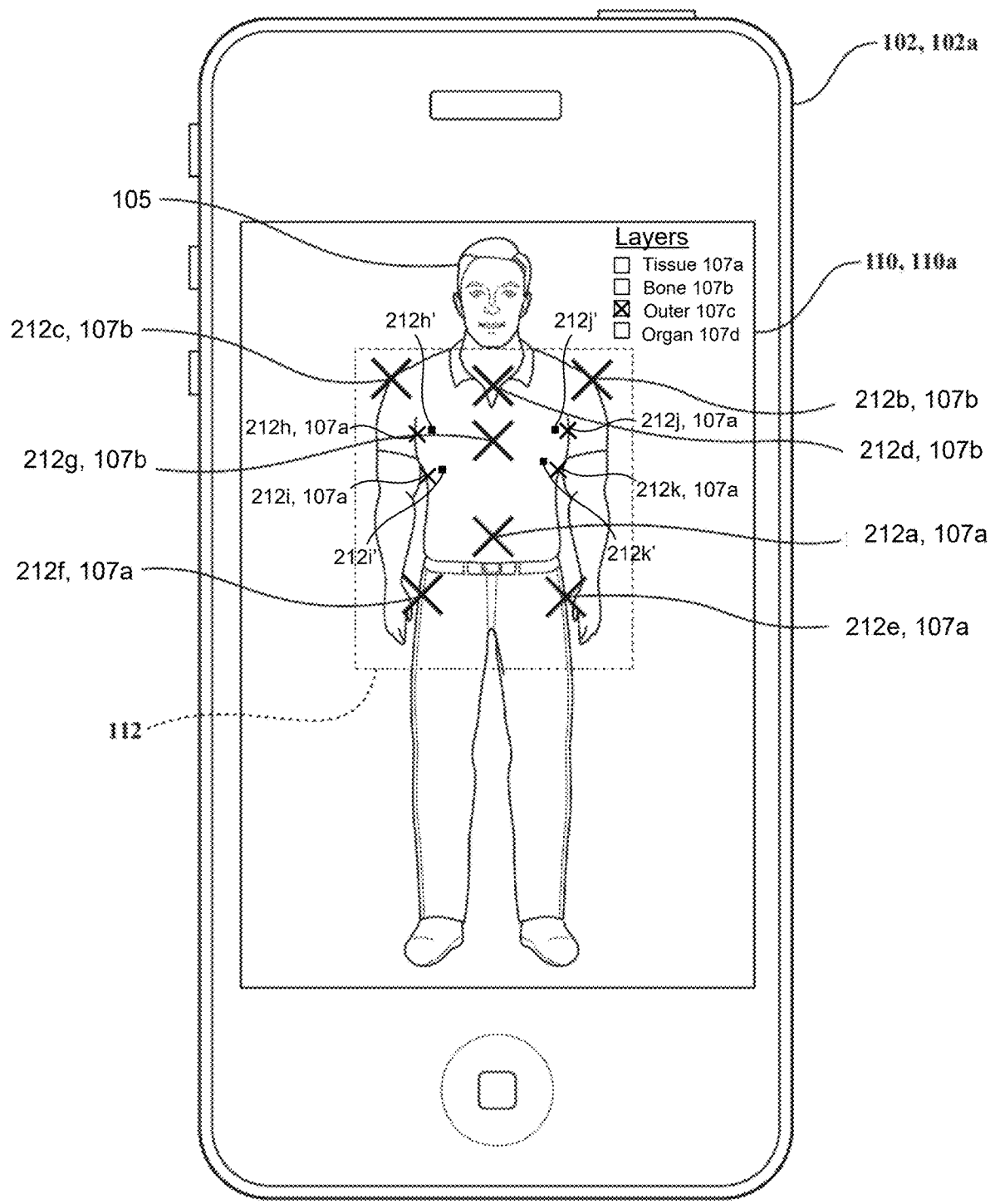
FIGS. 3A and 3B are schematic views of example visualizations of a target individual in a first state.

By being associated with a particular anatomical feature of the target individual 106, a reference marker 212 may also be associated with an anatomical layer 107 corresponding to that particular anatomical feature. For example, FIG. 3A depicts a reference marker 212 on each shoulder of the target individual 106. If the reference marker 212 was placed at the shoulder on the scapula, that reference marker 212, in referring to a bone, may be assigned to a layer 107 corresponding to the skeletal system (i.e., a layer 107 that includes the scapula bone). In contrast, if the reference marker 212 was placed at the rotator cuff, the reference marker 212 may be assigned a layer 107 corresponding to muscles/tendons such as a soft tissue layer 107. In some configurations, when the placement of the reference marker 212 may correspond to different anatomical features at or in close proximity to the placement location, the user 104 may be prompted by the AR system 200 to request that the user 104 specifies which specific anatomical feature was the intended target of the placement. For instance, in the example of the shoulder, the user 104 receives a prompt that requests the user 104 to indicate whether the reference marker 212 was intended for the rotator cuff or the scapula. Once the AR system 200 determines the target anatomical feature of the reference marker 212, the AR system 200 may assign a reference marker 212 to the anatomical layer 107 corresponding to the target anatomical feature for which it identifies. In some examples, instead of actively assigning the reference marker 212 to the reference layer 107, the AR system 200 is configured to have the reference marker 212 inherently assume the reference layer 107 corresponding to the target anatomical feature as a property of the reference marker 212.

In some implementations, the AR device 102 assigns the reference marker(s) 212 by detecting an input (e.g., touch, hand gesture, etc.) from the user 104 corresponding to one or more particular parts of the body of the target individual 106. In particular, the reference markers 212 may be identified by the user's 104 interaction with the AR device 102. For example, in some implementations, the user 104 touches the display 110a at locations corresponding to each reference marker 212. In other implementations, the AR device 102b receives an input from the user 104 via the camera 108b, or the trackpad 111 corresponding to each reference marker 212. For example, the camera 108b may capture the location of the user's 104 hand at locations corresponding to each reference marker 212.

In some implementations, the AR device 102 recognizes and assigns the reference marker(s) 212 to one or more particular parts of the body (e.g., facial features) of the target individual 106. In this respect, the reference markers 212 are capable of being computer-generated in addition or in alternative to being user-designated (i.e., manually assigned by the user 104). For example, the image capture device 108 may include an infrared camera that uses infrared laser scatter beam technology, for example, to recognize and assign the reference markers 212 to the one or more particular parts of the body (e.g., facial features) of the target individual 106. In particular, the image capture device 108 may be able to create a three-dimensional reference map of the face of the target individual 106 and compare the three-dimensional reference map to reference data stored in a storage resource of the AR device 102, such as the storage device 630 (FIG. 6). The AR device 102 may use the infrared camera of the image capturing device 108 to identify the reference markers 212 on the face of the target individual 106. The AR device 102 may identify the reference markers 212 on the lips, corners of the mouth, tip of the nose, or ears of the target individual 106. For example, the AR device 102 may identify the reference markers 212 based on input (e.g., touch, hand gesture, etc.) from the user 104. As will be explained in more detail below, in some implementations, the AR device 102 uses the identification information from the infrared camera, along with the identified referenced markers 212 based on the input from the user 104, to transmit data corresponding to the location of the reference markers 212 to a processing module (e.g., processor 610 of FIG. 6) to allow the AR device 102 to advantageously give more individualized and specific estimates of the location of various anatomical features on the body (e.g., face) of the target individual 106, including the underlying blood vessels, nerves, and muscles.

In some implementations, the AR device 102 identifies and assigns the reference marker(s) 30 by using machine learning or artificial intelligence algorithms to identify particular parts of the body of the target individual 106. The AR device 102 may assign the locations of the reference markers 212 on the target individual 106 based on the locations of similar reference markers 212 on one or more other target individuals 106. The AR device 102 may use machine learning or artificial intelligence algorithms to identify the target individual 106 as being a human body by detecting a silhouette of the target individual 106, recognizing body parts of the detected silhouette (e.g., limbs, crotch, armpits, or neck), and then determining the location of, and assigning, reference markers 30 based on the recognized body parts. In this regard, in some implementations, the AR device 102 may prompt the user to identify one or more particular reference points (e.g., body parts) on the target individual 106 prior to determining the location of, and assigning, reference markers 212 based on those body parts. In some configurations, the AR device 102 may utilize a scanning technology (e.g., laser imaging, detection, and ranging (Lidar), ultrasound, computed tomography, etc.) to identify one or more particular reference points (e.g., body parts) on the target individual 106 prior to determining the location of, and assigning, reference markers 212 based on those body parts.

Figure 3B:
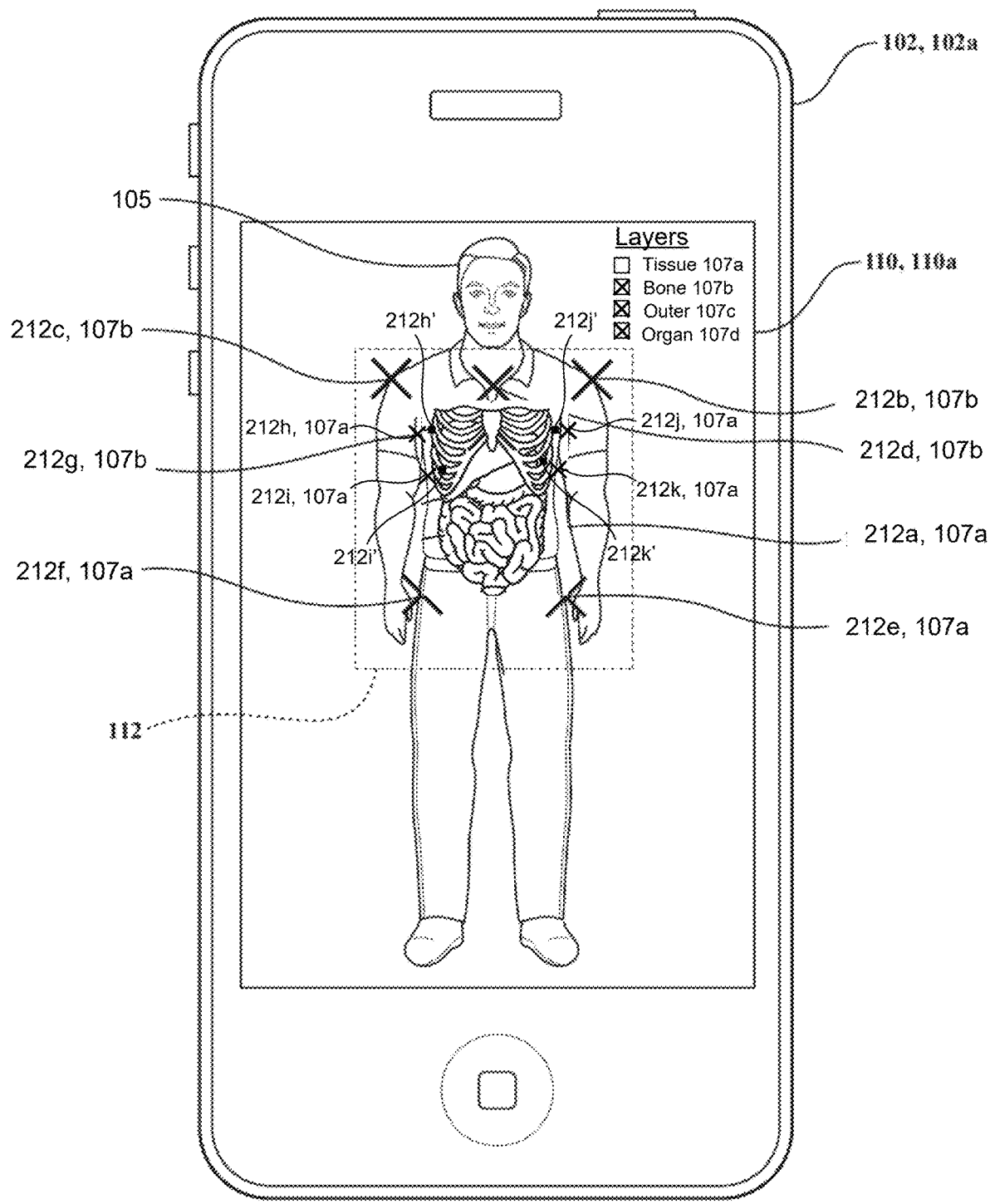
Figure 3C:
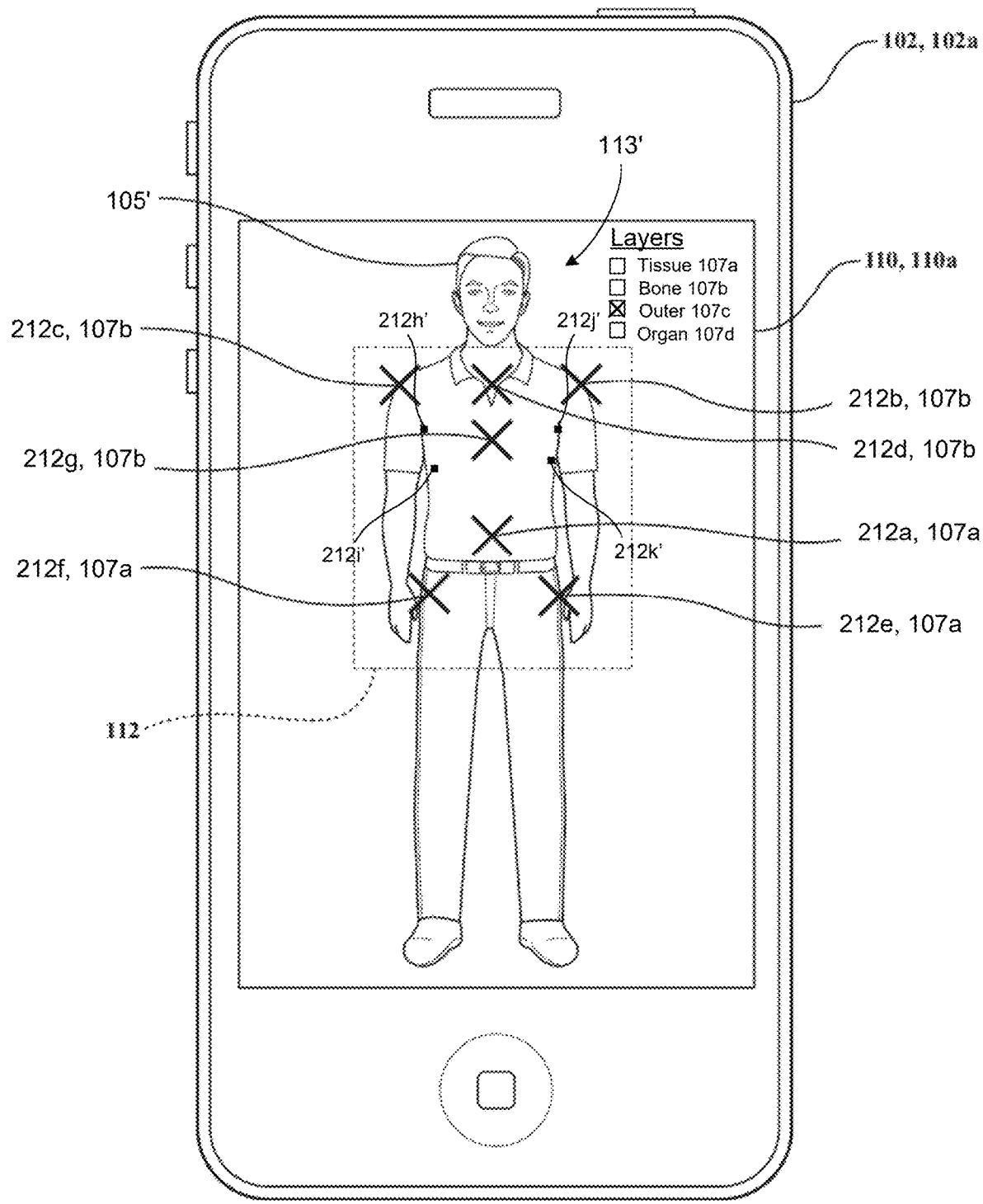
FIGS. 3C and 3D are schematic views of example visualizations of the target individual in a second state based on changes to the first state of FIGS. 3A and 3B.
Figure 3D:
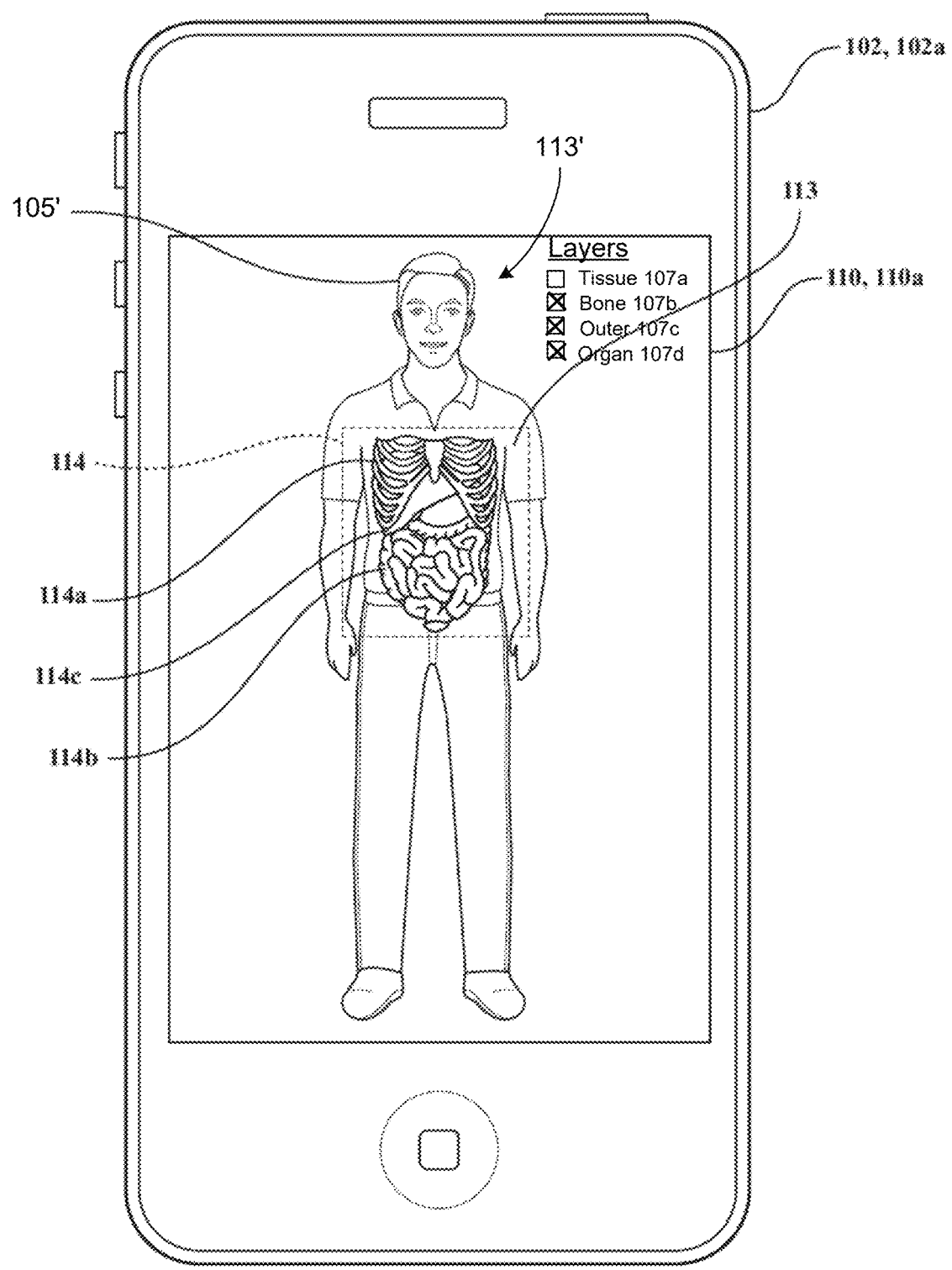

In FIGS. 3A-3D, the visual representation 103 of the target individual 106 includes a plurality of initial reference markers 212. The user 104 may then modify a set of the initial reference markers 212 to generate one or more modified or updated reference markers 212'. In these examples, there are eleven initial reference markers 212 212a-k shown in FIGS. 3A and 3B. FIGS. 3C and 3D then depict a visualization (e.g., a modified visual representation 105') of the predicted physical state for the target individual 106 in response to modifying four of the eleven initial reference markers 212 (e.g., modifying reference markers 212h-k). Each of these reference markers 212 may be associated with an anatomical layer 107. A first reference marker 212a corresponds to a navel of the target individual 106 and is associated with a soft tissue layer 107a. A second reference marker 212*b* corresponds to a portion of a right shoulder of the target individual 106 and is associated with a bone layer 107*b*. A third reference marker 212*c* corresponds to a portion of a left shoulder of the target individual 106 and is also associated with the bone layer 107*b*. A fourth reference marker 212*d* corresponds to a portion of a collarbone of the target individual 106 and is associated with the bone layer 107*b*. A fifth reference marker 212*e* corresponds to a portion of a left hip of the target individual 106 and is associated with the soft tissue layer 107*a*. A sixth reference marker 212*f* corresponds to a portion of a right hip of the target individual 106 and is associated with the soft tissue layer 107*a*. A seventh reference marker 212*g* corresponds to a portion of a sternum of the target individual 106 and is associated with the bone layer 107*b*. The eighth and ninth reference markers 212*h*, 212*i* correspond to fatty tissue around the left pectoral muscle of the target individual 106 and are associated with the soft tissue layer 107*a*. Similarly, the tenth and eleventh reference markers 212*j*, 212*k* correspond to fatty tissue around the right pectoral muscle of the target individual 106 and are also associated with the soft tissue layer 107*a*. Reference markers 212*a*-212*k* do not represent an exhaustive list of all reference markers 212, but rather an exemplary list of reference markers that may be identified by AR device 102. Furthermore, AR device 102 may add, remove, or otherwise identify other reference markers 212 at any time during the visualization of the target individual 106. For example, the user 104 may add other reference markers 212 such as reference markers 212 corresponding to a neck, a nose, eyes, a mouth, knees, ankles, a gluteal fold, shoulder blades, wrists, or elbows, without departing from the teachings herein. The AR device 102 and/or AR system 200 may also omit one or more reference markers 212*a*-212*k*, without departing from the teachings herein.

In some examples, the reference markers 212 and/or other anatomical data captured about the target individual 106 may be used by the AR system 200 to generate an anatomical profile of the target individual 106. The anatomical profile may include a plurality of characteristics corresponding to the individual 106. In some implementations, the anatomical profile includes or is based on a plurality of target data, such as age or sex of the target individual 106. In some implementations, the AR device 102 determines the anatomical profile based on an input (e.g., touch, hand gesture, etc.) from the user 104. In other implementations, the AR device 102 uses machine learning or artificial intelligence algorithms to determine the anatomical profile.

FIG. 3B is similar to FIG. 3A except that different anatomical layers 107 are active in FIG. 3A compared to FIG. 3B. That is, FIG. 3A depicts the visual representation 105 of the target individual 106 as a graphical representation 113 of an outer layer 107*c*. In other words, FIG. 3A illustrates the AR system 200 with the AR device 102 rendering a display of the target individual 106 being clothed such that all other layers 107 besides the outer layer 107*c* have been toggled off (e.g., by the user 104 or as an initial default view). In contrast, FIG. 3B shows that three layers 107 are toggled on. Namely, the outer layer 107*c*, the soft tissue layer 107*a*, and the bone layer 107*b* are active. With these layers 107 active, the user 104 can view or visualize inner anatomical features shown as a graphical representation 113 of the target individual 106.

As previously mentioned, FIGS. 3C and 3D illustrate an alternative (or modified) visual representation 105' of the target individual 106. Here, one or more graphical representations 113 forming the initial state of the target individual 106 as shown by the initial visual representation 105 in FIGS. 3A and 3B are modified by the AR system 200 to become modified graphical representations 113'. In the example shown in FIGS. 3A-3B, the target individual 106 has fatty tissue in his chest region that he would like removed or at least to visualize the removal of his fatty tissue. To perform this modification, the user 104 may move initial reference markers 212 from a first location to a second location different than the first location to generate a modified reference marker 212'. In this example, the eight, ninth, tenth, and eleventh initial reference markers 212*h-k* around the pectorals are moved towards the sternum to simulate the removal of the fatty tissue on each side of the chest resulting in the modified reference markers 212*h-k*'. In other words, the AR system 200 is being used by the user 104 to simulate or predict a future physical state of the target individual 106 if the fatty tissue was removed. In this respect the predicted figure physical state occurs in response to an anticipated change to the target individual 106 (e.g., facilitated by changes to and relations between reference markers 212).

Although FIGS. 3A-3D depict the AR system 200 modifying multiple reference markers 212, as few as one reference marker 212 may be modified to trigger a relationship differences between reference markers 212 (e.g., between an initial reference marker 212 and a modified reference marker 212') and allow the AR system 200 to predict a future physical state for the target individual 106 based on the change. For example, the AR system 200 changes a location of a first initial reference marker 212*a* relative to a location of a second reference marker 212*b* by moving the first reference marker 212*a* to a new location corresponding to reference marker 212*a*' and/or by moving the second reference marker 212*b* to a new location corresponding to reference marker 212*b*', such that a distance between reference markers 212*a*' and 212*b*' is different than a distance between reference markers 212*a* and 212*b*. In particular, the user 104 may instruct the AR system 200, via the input interface 210, to change a location of one or more of the reference markers 212 by interacting with the AR device 102 in the manner previously described (e.g., touch, hand gesture, etc.). In this regard, the user 104 may change the locations of reference markers 212' to indicate a change in target individual's future physical body state. For instance, a change in the location of one or more reference markers 112 indicates future weight loss, future weight gain, or future medical or cosmetic procedure (e.g., implant, removal, movement, etc. of material and/or part of the body of the target individual 106) that the target individual 106 will, or desires to, undergo.

In some implementations, the AR system 200 modifies an initial graphical representation 113 (e.g., one or more of the virtual images 114) to correspond to one or more anticipated changes to the target individual 106. For example, the AR system 200 may change a location, shape, size, and/or other characteristic of the initial graphical representation 113, such that a relationship (e.g., size ratio, distance, etc.) between the modified graphical representation 113' and the visual representation 105 of the target individual 106 is different than a relationship (e.g., size ratio, distance, etc.) between the initial graphical representation 113 and the visual representation 105. In particular, the user 104 may instruct the AR system 200, via the input interface 210, to change a characteristic (e.g., size, shape, location, etc.) of one or more anatomical features via the virtual images 114 by interacting with the AR device 102 in the manner previously described (e.g., touch, hand gesture, etc.). For instance, these modifications by the user 104 may occur by using a finger or stylus to draw on the display 110 or in the environment 100 such that the AR device 102 can recognize the drawing motions. When the user 104 draws the modifications, the drawing may indicate the boundary of a modified virtual image or identify reference markers 212 along the boundary of the modified virtual image 114'. In some configurations, the user 104 selects a preprogrammed modification such that the selection executes instructions to change a selected object or region in a preconfigured operations. For instance, the user 104 selects the target individual's liver and selects an enlargement operation (e.g., an enlargement icon with a slider to set the enlargement scale). By any of these approaches, the result is referred to as a modified virtual image because the initial virtual image representing one or more anatomical features has been altered. In this regard, the location, shape, size, and/or other characteristic of the initial virtual images 114' may be altered to form the modified virtual image. For instance, a modified image may be used to represent a change in target individual's future physical body state (future weight loss, future weight gain, or future medical or cosmetic procedure (e.g., implant, removal, movement, etc. of material and/or part of the body of the target individual 106) that the target individual 106 will, or desires to, undergo).

The AR device 102 may determine an alternative visual representation 105' of the target individual 106 based on the initial reference markers 212, the modified reference markers 212', the initial graphical representation 113, and/or the graphical representation 113' (e.g., virtual images 114). As illustrated in FIGS. 3C and 3D, similar to the visual representation 105 of FIGS. 3A and 3B, the AR system 200 may determine an anatomical profile of the target individual 106 based now on the changes to the reference markers 212 (e.g., the creation of modified reference markers 212'). The anatomical profile may include a plurality of characteristics corresponding to unchanged initial reference markers 212 (e.g., if any are still present) and/or the modified reference markers 212'. As described above, the anatomical profile may be based on a plurality of target data, input from the user 104, or machine learning or artificial intelligence algorithms. In some implementations, the anatomical profile may also be based on certain changes that the target individual 106 may undergo, such as the changes to the reference markers 212 (i.e., the generation of modified reference markers 212').

FIGS. 3C and 3D show the first AR device 102a displaying the alternative visual representation 105' of the target individual 106 on the display 110 (e.g., the first display 110a). As part of the visualization of the target individual 106, the AR device 102 displays the modified graphical representation 113' of the target individual 106, where the modified graphical representation 113', much like the graphical representation 113 as previously described, includes virtual images 114 (e.g., reference image files 252) of anatomical features. Here, since the alternative visual representation 105' occurs in response to changes in the reference markers 212 and the reference markers 212 drive the generation of the graphical representation 115 (e.g., by scaling or otherwise modifying the reference image files 252), the modified graphical representation 113' is the representation of virtual images (e.g., the reference image files 252) that have been adapted as determined by the AR system 200 to correspond to the reference markers 212 that include the modified reference markers 212'. In other words, the modified graphical representation 113' when compared to the graphical representation 113 embodies the changes to the reference markers 212. In this respect, the modified graphical representation 113' is capable of corresponding to different future physical states of the target individual 106 to represent state changes such as weight loss, weight gain, becoming pregnant, procedural changes (e.g., undergoing reconstructive or cosmetic surgery), or other changes that a body may undergo.

FIG. 3D when contrasted with FIG. 3C illustrates that a predicted future physical state of the target individual 106 (e.g., based on changes to reference markers 212) may impact one or more layers 107. More particularly, that this impact can occur to layers 107 that do not necessarily correspond to the layer 107 associated with a modified reference marker 212'. For instance, as shown in FIG. 3D, simulated changes to the soft tissue layer 107a (e.g., the removal of fatty tissue in the chest region) results in a modified graphical representation 113' of anatomical features on other layers 107. Here, FIG. 3D illustrates that the rib cage may shift slightly based on the removal of fatty tissue in the chest region. For example, the fatty tissue, when present may generate additional weight on the rib cage that compresses it to come degree. Therefore, removal of the fatty tissue may allow the rib cage, and particularly certain ribs, to shift to a resting position that is under less compression stress. The AR system 200 is able to identify this change to other anatomical features because the relative dimensions of the reference markers 212 indicate not only how the soft tissue layer 107 may be graphically represented, but also how other layers 107 are graphically represented. Therefore, when the user 104 generates the modified reference markers 212' the modified reference markers 212 impact the how virtual images 114 (e.g., the reference image files 252) on all layers 107 may be represented as a graphical representation (e.g., the modified graphical representation 113').

With the ability to predict future physical states, a user 104, such as a healthcare professional, is able to identify the location of the inner anatomical features without performing conventional procedures such as an x-ray, an MRI or other medical scanning operations. Such a display is helpful in assisting the healthcare professional with identifying, within a reasonable degree of accuracy, a medical condition, a location for an incision, an organ, specific portion of a muscle or tendon, or any other interior anatomic structure not externally visible. For example, a patient is experiencing abdominal pain and points to the location of the pain on his or her body. The healthcare professional may then be able to better identify the issue by referencing where the pain is with respect to the location of the inner anatomical features (which is displayed in the graphical representation 113), such as distinguishing between a pain located at the duodenum as opposed to the pancreas, the pancreatic duct or the like. Accordingly, the AR device 102 and/or the AR system 200 assists the surgeon with treatment, diagnosis, patient education and the like without having to subject the patient to an x-ray, MRI or other internally invasive scanning procedures.

Figure 4C:
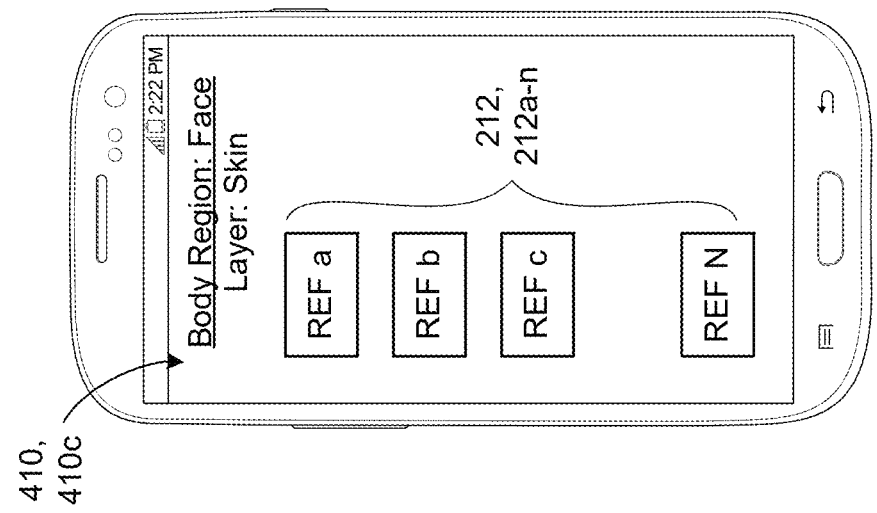
FIGS. 4A-4C are schematic views of example menus for the augmented reality system of FIG. 2.
Figure 4B:
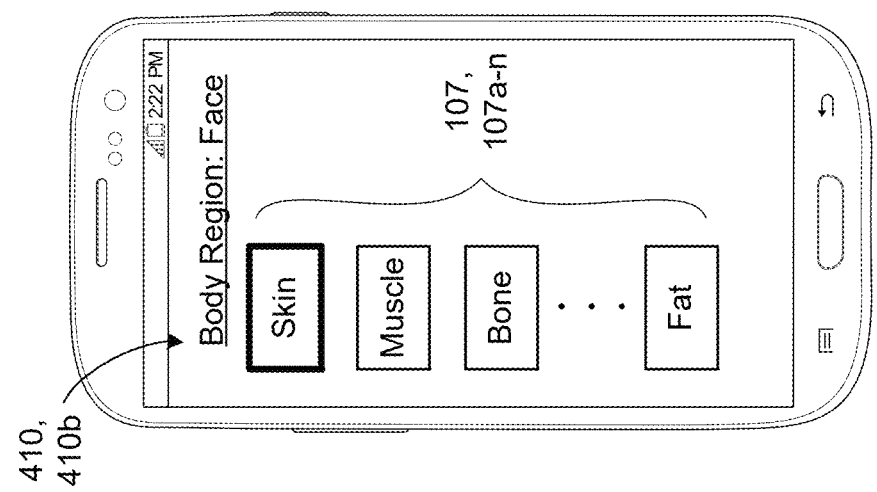
Figure 4A:
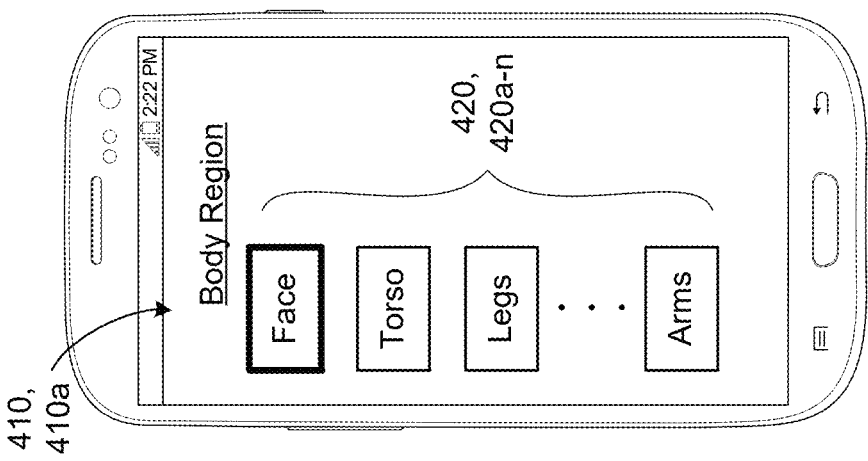

The AR system 200 may be configured with a wide range of navigation capabilities that enable the AR system 200 to display the visualization of the target individual 106. For example, the user 104 of the AR device 102 may use the AR system 200 to focus on a body region of the target individual 106, an anatomical layer 107 for the target individual 106, and/or a specific reference marker 212. In this respect FIGS. 4A-4C illustrate a plurality of navigation panes or menus 410 that enable the user 104 to perform the functionality of the AR system 200 and to interact with that functionality in order to generate a desired representation of the target individual 106. In some implementations, these menus 410 are hierarchical in nature such that the user 104 can isolate a particular set of reference marker 212 by first selecting a body region 420 or a layer 107 where the set of reference markers 212 are located. For example, referring to FIG. 4A, the visualization of the target individual 106 may be divided into one or more body regions 420, 420a-n. Accordingly, the AR system 200 may render a first menu 410a that allows the user 104 to isolate one or more specific body regions 420. Here, as shown by the darker outline around the box for the face region, the user 104 has selected the face region 420 in order to in some way isolate or filter aspects of the face region of the visualization of the target individual 106. For instance, with the face region 420 selected, the user 104 may decide to use a second menu 410b corresponding to anatomical layers 107 for the target individual 106. In this respect, the user 104 may further filter the body region (e.g., the face region) by anatomical layers 107 within the body region 420. In some configurations, the user 104 may filter or isolate a layer 107 without first selecting a body region 420. In other words, the user 104 may use the layer menu 410b to view a layer 107 with respect to all body regions 420. Additionally or alternatively, the user 104 may select a reference marker 212 using a third menu 410c that corresponds to reference markers 212. Here, the AR system 200 may be configured to pre-filter the list of reference markers 212 using one or more other menus 410a, 410b. For example, in FIG. 4C, the user 104 has filtered a list of reference markers 212a-n by body region 420 (e.g., the face region) and anatomical layer 107 (e.g., the skin layer). Therefore, by using one or more menus 410 associated with the AR system 200, the user 104 may navigate the visualization to perform edits or changes (e.g., additions or removals). For instance, with the combination of menus 410, the user 104 can interact with the body of the target individual in a hierarchical manner according to body region, layer 107, and/or reference marker 212.

Figure 5:
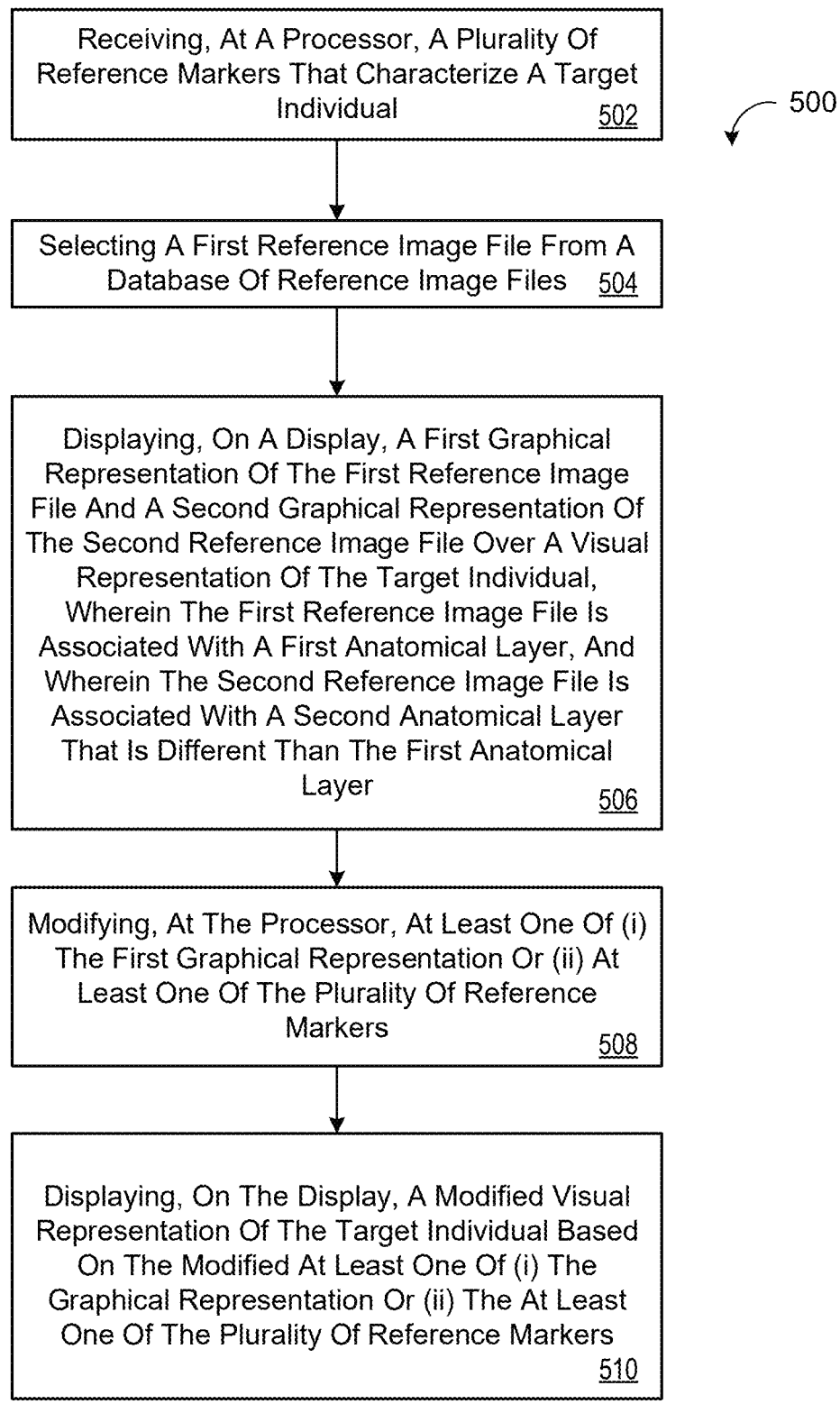
FIG. 5 is a flow diagram of an example method of displaying a visual representation of the target individual.

FIG. 5 is a flow chart illustrating a method 500 for displaying augmented anatomical features in accordance with an example implementation of the disclosed technology. At operation 502, the method 500 receives a plurality of reference markers 212 that characterize a target individual 106. At operations 504, the method 500 selects a first reference image file 252 and a second reference image file 252 from a database 250 of reference image files 252. At operation 506, the method 500 displays, on a display 110, a first graphical representation 113 of the first reference image file 252 and a second graphical representation 113 of the second reference image file 252 over a visual representation 103 of the target individual 106. The first reference image file 252 is associated with a first anatomical layer 107 and the second reference image file 252 is associated with a second anatomical layer 107 that is different than the first anatomical layer 107. At operation 508, the method 500 modifies at least one of (i) the first graphical representation 113 or (ii) at least one of the plurality of reference markers 212. At operation 510, the method 500 displays, on the display 110, a modified visual representation of the target individual 106 based on the modified at least one of (i) the first graphical representation 113 or (ii) the at least one of the plurality of reference markers 212.

FIG. 6 is schematic view of an example computing device 600 that may be used to implement the systems (e.g., the AR system 200) and methods (e.g., method 500) described in this document. The computing device 600 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 600 includes a processor 610, memory 620, a storage device 630, a high-speed interface/controller 640 connecting to the memory 620 and high-speed expansion ports 650, and a low speed interface/controller 660 connecting to a low speed bus 670 and a storage device 630. Each of the components 610, 620, 630, 640, 650, and 660, are interconnected using various busses, and may be mounted on a common motherboard or in other manners as appropriate. The processor 610 can process instructions for execution within the computing device 600, including instructions stored in the memory 620 or on the storage device 630 to display graphical information for a graphical user interface (GUI) on an external input/output device, such as display 680 coupled to high speed interface 640. In other implementations, multiple processors and/or multiple buses may be used, as appropriate, along with multiple memories and types of memory. Also, multiple computing devices 600 may be connected, with each device providing portions of the necessary operations (e.g., as a server bank, a group of blade servers, or a multi-processor system).

The network may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a fifth generation (5G) network a satellite communications network, and other communication networks. The network 208 may include one or more of a Wide Area Network (WAN), a Local Area Network (LAN), and a Personal Area Network (PAN). In some examples, the network includes a combination of data networks, telecommunication networks, or a combination of data and telecommunication networks. An augmented reality device 102 and augmented reality module 20 communicate with each other by sending and receiving signals (wired or wireless) via the network 208. In some examples, the network 208 provides access to cloud computing resources, which may be elastic/on-demand computing and/or storage resources available over the network 208. The term 'cloud' services generally refers to a service performed not locally on a user's device (e.g., device 102), but rather delivered from one or more remote devices accessible via one or more networks 208.

The memory 620 stores information non-transitorily within the computing device 600. The memory 620 may be a computer-readable medium, a volatile memory unit(s), or non-volatile memory unit(s). The non-transitory memory 620 may be physical devices used to store programs (e.g., sequences of instructions) or data (e.g., program state information) on a temporary or permanent basis for use by the computing device 600. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 630 is capable of providing mass storage for the computing device 600. In some implementations, the storage device 630 is a computer-readable medium. In various different implementations, the storage device 630 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 620, the storage device 630, or memory on processor 610.

The high speed controller 640 manages bandwidth-intensive operations for the computing device 600, while the low speed controller 660 manages lower bandwidth-intensive operations. Such allocation of duties is exemplary only. In some implementations, the high-speed controller 640 is coupled to the memory 620, the display 680 (e.g., through a graphics processor or accelerator), and to the high-speed expansion ports 650, which may accept various expansion cards (not shown). In some implementations, the low-speed controller 660 is coupled to the storage device 630 and a low-speed expansion port 690. The low-speed expansion port 690, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 600 may be implemented in a number of different forms, as shown in the figure. For example, it may be implemented as a standard server 600a or multiple times in a group of such servers 600a, as a laptop computer 600b, or as part of a rack server system 600c.

Among other advantages, the present disclosure provides methods, user devices, and systems for displaying augmented anatomical features. An augmented reality device may overlay virtual images of anatomy on top of the human body illustrate an approximation of the structures, tissues or organs that lie beneath the surface of an individual, such as a target individual, in front of a user, such as a healthcare professional. The virtual images can be adjusted to fit the target individual. The user may use the augmented reality device to identify certain anatomical reference points on the body of the target individual, and use those points to anchor and adjust the virtual images over the target individual. The virtual images may be representative of human anatomy of a human of similar age, sex, etc.

Among other advantages, the present disclosure also provides a method, user device, and system that does not require input of data files from outside imaging (e.g., x-ray, magnetic resonance imaging, computed tomography scan, etc.). Such files may have incompatible formats, be large and unwieldy, or require a large amount of processing power for each target individual.

Among other advantages, the present disclosure also provides a method, user device, and system that may be for general use. In this regard, use of the augmented reality device may not be restricted to certified healthcare providers. Furthermore, the expectation of the augmented reality device may be to output or display a computer-generated approximation of a representative human anatomy.

Among other advantages, the present disclosure also provides broad applicability. The augmented reality device may be in constant and rapid use with one target individual after another, and without requiring the input of outside data.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The following Clauses provide an exemplary configuration for a skimmer assembly and related methods, as described above.

Clause 1: A method comprising: receiving, at a processor, a plurality of reference markers that characterize a target individual; selecting a first reference image file and a second reference image file from a database of reference image files; displaying, on a display, a first graphical representation of the first reference image file and a second graphical representation of the second reference image file over a visual representation of the target individual, wherein the first reference image file is associated with a first anatomical layer, and wherein the second reference image file is associated with a second anatomical layer that is different than the first anatomical layer; modifying, by the processor, at least one of (i) the first graphical representation or (ii) at least one of the plurality of reference markers; and displaying, on the display, a modified visual representation of the target individual based on the modified at least one of (i) the first graphical representation or (ii) the at least one of the plurality of reference markers.

Clause 2: The method of clause 1, further comprising modifying, by the processor, the first reference image file based on the plurality of reference markers.

Clause 3: The method of clause 2, wherein displaying, on the display, the first graphical representation of the first reference image file over the visual representation of the target individual includes displaying the modified first reference image.

Clause 4: The method of any of clauses 1 through 3, wherein the first reference image file corresponds to at least one inner anatomical feature.

Clause 5: The method of clause 4, wherein the at least one inner anatomical feature includes a bone, an organ, or fat.

Clause 6: The method of any of clauses 1 through 5, wherein selecting the first reference image file and the second reference image file from the database of reference image files comprises: determining a relationship among the plurality of reference markers; and identifying that, from among the reference image files, at least one of the first reference image file or the second reference image file most closely matches the relationship.

Clause 7: The method of any of clauses 1 through 6, further comprising: modifying, by the processor, the second graphical representation of the second reference image file; and updating, on the display, the modified visual representation of the target individual based on the modified second graphical representation of the second reference image file.

Clause 8: The method of any of clauses 1 through 7, further comprising displaying, on the display, the first graphical representation of the first reference image file over the first graphical representation of the second reference image file.

Clause 9: The method of clause 8, wherein displaying the first graphical representation of the first reference image file over the second graphical representation of the second reference image file further comprises determining that the first anatomical layer associated with the first reference image file is closer to an outer anatomical layer than the second anatomical layer associated with the second reference image file.

Clause 10: The method of any of clauses 1 through 9, wherein each of the first graphical representation of the first reference image file and the second graphical representation of the second reference image file are selectably removable and selectably insertable by a user while viewing the modified visual representation of the target individual on the display.

Clause 11: A system comprising: a display; data processing hardware in communication with the display; and memory hardware in communication with the data processing hardware, the memory hardware storing instructions that, when executed on the data processing hardware, cause the data processing hardware to perform operations including: receiving a plurality of reference markers that characterize a target individual; selecting a first reference image file and a second reference image file from a database of reference image files; displaying, on the display, a first graphical representation of the first reference image file and a second graphical representation of the second reference image file over a visual representation of the target individual, wherein the first reference image file is associated with a first anatomical layer, and wherein the second reference image file is associated with a second anatomical layer that is different than the first anatomical layer; modifying at least one of (i) the first graphical representation or (ii) at least one of the plurality of reference markers; and displaying, on the display, a modified visual representation of the target individual based on the modified at least one of (i) the first graphical representation or (ii) the at least one of the plurality of reference markers.

Clause 12: The system of clause 11, wherein the operations further comprise modifying the first reference image file based on the plurality of reference markers.

Clause 13: The system of clause 12, wherein displaying, on the display, the first graphical representation of the first reference image file over the visual representation of the target individual includes displaying the modified first reference image.

Clause 14: The system of any of clauses 11 through 13, wherein the first reference image file corresponds to at least one inner anatomical feature.

Clause 15: The system of clause 14, wherein the at least one inner anatomical feature includes a bone, an organ, or fat.

Clause 16: The system of any of clauses 11 through 15, wherein selecting the first reference image file and the second reference image file from the database of reference image files comprises: determining a relationship among the plurality of reference markers; and identifying that, from among the reference image files, at least one of the first reference image file or the second reference image file most closely matches the relationship.

Clause 17: The system of any of clauses 11 through 16, wherein the operations further comprise: modifying the second graphical representation of the second reference image file; and updating, on the display, the modified visual representation of the target individual based on the modified second graphical representation of the second reference image file.

Clause 18: The system of any of clauses 11 through 17, wherein the operations further comprise displaying the first graphical representation of the first reference image file over the first graphical representation of the second reference image file.

Clause 19: The system of clause 18, wherein displaying the first graphical representation of the first reference image file over the second graphical representation of the second reference image file further comprises determining that the first anatomical layer associated with the first reference image file is closer to an outer anatomical layer than the second anatomical layer associated with the second reference image file.

Clause 20: The system of any of clauses 11 through 19, wherein each of the first graphical representation of the first reference image file and the second graphical representation of the second reference image file are selectably removable and selectably insertable by a user while viewing the modified visual representation of the target individual on the display.

A number of implementations have been described. Nevertheless, it will be understood that various modifications may be made without departing from the spirit and scope of the disclosure. Accordingly, other implementations are within the scope of the following claims.

What is claimed is:

1. A method comprising:
   receiving, at a processor, a plurality of reference markers that characterize a target individual;
   selecting a first reference image file and a second reference image file from a database of reference image files;
   displaying, on a display, a first graphical representation of the first reference image file and a second graphical representation of the second reference image file over a visual representation of the target individual, wherein the first reference image file is associated with a first anatomical layer, and wherein the second reference image file is associated with a second anatomical layer that is different than the first anatomical layer;
   modifying, by the processor, a reference marker of the plurality of reference markers by moving the reference marker from an initial location to a new location;
   determining a difference between the initial location and the new location; and
   in response to determining the difference between the initial location and the new location, displaying, on the display, a modified visual representation of the target individual.

2. The method of claim 1, further comprising modifying, by the processor, the first reference image file based on the modified reference marker.

3. The method of claim 2, wherein displaying, on the display, the first graphical representation of the first reference image file over the visual representation of the target individual includes displaying the modified first reference image.

4. The method of claim 1, wherein the first reference image file corresponds to at least one inner anatomical feature.

5. The method of claim 4, wherein the at least one inner anatomical feature includes a bone, an organ, or fat.

6. The method of claim 1, wherein selecting the first reference image file and the second reference image file from the database of reference image files comprises:
   determining a relationship among the plurality of reference markers; and
   identifying that, from among the reference image files, at least one of the first reference image file or the second reference image file most closely matches the relationship.

7. The method of claim 1, further comprising:
   modifying, by the processor, the second graphical representation of the second reference image file; and
   updating, on the display, the modified visual representation of the target individual based on the modified second graphical representation of the second reference image file.

8. The method of claim 1, further comprising displaying, on the display, the first graphical representation of the first reference image file over the first graphical representation of the second reference image file.

9. The method of claim 8, wherein displaying the first graphical representation of the first reference image file over the second graphical representation of the second reference image file further comprises determining that the first anatomical layer associated with the first reference image file is closer to an outer anatomical layer than the second anatomical layer associated with the second reference image file.

10. The method of claim 1, wherein each of the first graphical representation of the first reference image file and the second graphical representation of the second reference image file are selectably removable and selectably insertable by a user while viewing the modified visual representation of the target individual on the display.

11. The method of claim 1, wherein modifying the reference marker includes positioning the reference marker at the new location based on a gesture from a user captured within an environment of the target individual.

12. A system comprising:
   a display;
   data processing hardware in communication with the display; and
   memory hardware in communication with the data processing hardware, the memory hardware storing instructions that, when executed on the data processing hardware, cause the data processing hardware to perform operations including:
   receiving a plurality of reference markers that characterize a target individual;

selecting a first reference image file and a second reference image file from a database of reference image files;

displaying, on the display, a first graphical representation of the first reference image file and a second graphical representation of the second reference image file over a visual representation of the target individual, wherein the first reference image file is associated with a first anatomical layer, and wherein the second reference image file is associated with a second anatomical layer that is different than the first anatomical layer;

modifying a reference marker of the plurality of reference markers by moving the reference marker from an initial location to a new location;

determining a difference between the initial location and the new location; and in response to determining the difference between the initial location and the new location, displaying, on the display, a modified visual representation of the target individual.

13. The system of claim 12, wherein the operations further comprise modifying the first reference image file based on the modified reference marker.

14. The system of claim 13, wherein displaying, on the display, the first graphical representation of the first reference image file over the visual representation of the target individual includes displaying the modified first reference image.

15. The system of claim 12, wherein the first reference image file corresponds to at least one inner anatomical feature.

16. The system of claim 15, wherein the at least one inner anatomical feature includes a bone, an organ, or fat.

17. The system of claim 12, wherein selecting the first reference image file and the second reference image file from the database of reference image files comprises:
determining a relationship among the plurality of reference markers; and
identifying that, from among the reference image files, at least one of the first reference image file or the second reference image file most closely matches the relationship.

18. The system of claim 12, wherein the operations further comprise:
modifying the second graphical representation of the second reference image file; and
updating, on the display, the modified visual representation of the target individual based on the modified second graphical representation of the second reference image file.

19. The system of claim 12, wherein the operations further comprise displaying the first graphical representation of the first reference image file over the first graphical representation of the second reference image file.

20. The system of claim 19, wherein displaying the first graphical representation of the first reference image file over the second graphical representation of the second reference image file further comprises determining that the first anatomical layer associated with the first reference image file is closer to an outer anatomical layer than the second anatomical layer associated with the second reference image file.

21. The system of claim 12, wherein each of the first graphical representation of the first reference image file and the second graphical representation of the second reference image file are selectably removable and selectably insertable by a user while viewing the modified visual representation of the target individual on the display.

* * * * *